US008329011B2

(12) United States Patent
Nomoto et al.

(10) Patent No.: US 8,329,011 B2
(45) Date of Patent: Dec. 11, 2012

(54) POLYMERASE-IMMOBILIZED ELECTRODE

(75) Inventors: Tsuyoshi Nomoto, Tokyo (JP); Wataru Kubo, Inagi (JP)

(73) Assignee: Canon Kabushiki Kaisha, Tokyo (JP)

( * ) Notice: Subject to any disclaimer, the term of this patent is extended or adjusted under 35 U.S.C. 154(b) by 1025 days.

(21) Appl. No.: 12/297,173

(22) PCT Filed: Jun. 18, 2007

(86) PCT No.: PCT/JP2007/062646

§ 371 (c)(1),
(2), (4) Date: Oct. 14, 2008

(87) PCT Pub. No.: WO2007/148809

PCT Pub. Date: Dec. 27, 2007

(65) Prior Publication Data

US 2009/0134042 A1 May 28, 2009

(30) Foreign Application Priority Data

Jun. 20, 2006 (JP) ................................. 2006-170240

(51) Int. Cl.
*C12N 11/00* (2006.01)
*C12N 11/06* (2006.01)

(52) U.S. Cl. ................... 204/403.14; 435/174; 435/176; 435/177

(58) Field of Classification Search .................. 204/418, 204/403.01; 205/777.5; 435/6.11, 6.3, 174, 435/176, 177
See application file for complete search history.

(56) References Cited

U.S. PATENT DOCUMENTS

| | | | |
|---|---|---|---|
| 5,633,366 | A | 5/1997 | Takamatsu et al. |
| 6,424,418 | B2 | 7/2002 | Kawabata et al. |
| 7,235,396 | B2 | 6/2007 | Nomoto et al. |
| 7,354,995 | B2 | 4/2008 | Imamura et al. |
| 7,399,644 | B2 | 7/2008 | Homma et al. |

(Continued)

FOREIGN PATENT DOCUMENTS

| | | |
|---|---|---|
| EP | 0251786 | 1/1988 |

(Continued)

OTHER PUBLICATIONS

Matsuno et al. Direct Monitoring Kinetic Studies of DNA Polymerase Reactions on a DNA-Immobilized Quartz-Crystal Microbalance, Cehm Eur. J. 2001, 7, 3305-3312.* PCT International Search Report and Written Opinion of the Inter-national Searching Authority in International Application No. PCT/JP2007/062646, Mailing Date Sep. 25, 2007.

F. Sanger, et al., "DNA Sequencing with chain-terminating inhibitors", Proc. Natl. Acad. Sci. USA, 1977, pp. 5463-5467, vol. 74, No. 12.

R. Finn, et al., "Pfam: clans, web tools and services", Nucleic Acids Research, 2006, pp. D247-D251, vol. 34.

M. Gruen, et al., "Synthesis of 2'IODO and 2'BROMO-ATP and GTP Analogues as Potential Phasing Tools for X-Ray Crystallography", Nucleosides, Nucleotides, and Nucleic Acids, 1999, pp. 137-151, vol. 18, No. 1.

(Continued)

*Primary Examiner* — Alex Noguerola
*Assistant Examiner* — Gurpreet Kaur
(74) *Attorney, Agent, or Firm* — Fitzpatrick, Cella, Harper & Scinto

(57) ABSTRACT

The present invention is to reduce a false signal in an apparatus for electrochemically decoding a base sequence of DNA, which false signal is caused by a phenomenon that even unreacted nucleotide 5'-triphosphate derivatives remaining in the solution are electrochemically converted on an electrode. The present invention provides a polymerase-immobilized electrode that comprises an electroconductive substrate and a polymerase unit immobilized on the surface of the electroconductive substrate, wherein the polymerase unit comprises a polymerase part, an anchor part and an electroconductive part, which are linked in an order of the polymerase part, the anchor part and the electroconductive part, or in an order of the polymerase part, the electroconductive part and the anchor part; and the polymerase unit is immobilized on the electroconductive substrate by the anchor part; wherein a free end of the electroconductive part, not immobilized on the electroconductive substrate, is located in the vicinity of an active site of the polymerase part.

7 Claims, 8 Drawing Sheets

1
3
4
9
2
5

U.S. PATENT DOCUMENTS

| | | | | |
|---|---|---|---|---|
| 2004/0014054 | A1* | 1/2004 | Frey et al. | 435/6 |
| 2005/0042633 | A1* | 2/2005 | Williams | 435/6 |
| 2006/0172398 | A1 | 8/2006 | Nomoto et al. | |
| 2006/0172399 | A1 | 8/2006 | Nomoto et al. | |
| 2006/0275811 | A1 | 12/2006 | Hatakeyama et al. | |
| 2007/0131546 | A1 | 6/2007 | Nomoto et al. | |
| 2007/0131547 | A1 | 6/2007 | Nomoto et al. | |
| 2007/0190590 | A1 | 8/2007 | Kubo et al. | |
| 2008/0108123 | A1 | 5/2008 | Imamura et al. | |

FOREIGN PATENT DOCUMENTS

| | | |
|---|---|---|
| JP | 5-168500 | 7/1993 |
| JP | 7-97391 | 4/1994 |
| JP | 8-5908 | 1/1996 |
| JP | 2002-513592 | 5/2002 |
| JP | 2003-189899 | 7/2003 |
| JP | 2004-20386 | 1/2004 |
| WO | 99-57319 | 11/1999 |

OTHER PUBLICATIONS

U.S. Appl. No. 11/913,047, filed Oct. 29, 2007.

U.S. Appl. No. 11/913,045, filed Oct. 29, 2007.

U.S. Appl. No. 12/093,138, filed May 8, 2008.

U.S. Appl. No. 10/548,442, filed Mar. 14, 2008.

PCT International Preliminary Report on Patentability in International Application No. PCT/JP2007/062646, Mailing Date Jan. 8, 2009.

* cited by examiner

TARGET DNA
NUCLEOTIDE TRIPHOSPHATE DERIVATIVES EACH OF WHICH IS CAPPED WITH AN ELECTROCHEMICALLY CONVERTIBLE STRUCTURE
POLYMERASE
PRIMER (ELONGATING DNA)

3' - G~AACATX1X2X3X4X5X6 ---- 5'
5' C~TTGTAY 3'

3' - G~AACATX1X2X3X4X5X6 ---- 5'
5' - C~TTGTAY 3'

SEQUENCE LISTING

```
<160> NUMBER OF SEQ ID NOS: 18

<210> SEQ ID NO 1
<211> LENGTH: 30
<212> TYPE: DNA
<213> ORGANISM: Artificial
<220> FEATURE:
<223> OTHER INFORMATION: primer

<400> SEQUENCE: 1

aataatcata tgatcgtttc tgacatcgaa                                      30


<210> SEQ ID NO 2
<211> LENGTH: 30
<212> TYPE: DNA
<213> ORGANISM: Artificial
<220> FEATURE:
<223> OTHER INFORMATION: primer

<400> SEQUENCE: 2

aataatggat cctcagtggc aaatcgccca                                      30


<210> SEQ ID NO 3
<211> LENGTH: 6694
<212> TYPE: DNA
<213> ORGANISM: Artificial
<220> FEATURE:
<223> OTHER INFORMATION: plasmid vector, pET-14-T7g5(D28)

<400> SEQUENCE: 3

ttctcatgtt tgacagctta tcatcgataa gctttaatgc ggtagtttat cacagttaaa      60

ttgctaacgc agtcaggcac cgtgtatgaa atctaacaat gcgctcatcg tcatcctcgg     120

caccgtcacc ctggatgctg taggcatagg cttggttatg ccggtactgc cgggcctctt     180

gcgggatatc gtccattccg acagcatcgc cagtcactat ggcgtgctgc tagcgctata     240

tgcgttgatg caatttctat gcgcacccgt tctcggagca ctgtccgacc gctttggccg     300

ccgcccagtc ctgctcgctt cgctacttgg agccactatc gactacgcga tcatggcgac     360

cacacccgtc ctgtggatat ccggatatag ttcctccttt cagcaaaaaa cccctcaaga     420

cccgtttaga ggccccaagg ggttatgcta gttattgctc agcggtggca gcagccaact     480

cagcttcctt tcgggctttg ttagcagccg gatcctcagt ggcaaatcgc ccaattagga     540

cccatcttac cttcggtatc cagaagacac cggaagttcc agtggtctcc aacccagcgc     600

atcgcttctt gtgcggtctc aatgaccacc tgagcaatct cttcggtacg gcagcctact     660

tggatttcat catgtaccca tgccatgtac gcaaagtccc catcccagcc atgcttcaag     720

cctttctcta cgagcatctc ttcggtcttg ataatccaca gtttgcagat gagagcacca     780

gcagattgca gtagggtatt caaggcagcg tgaggactac gaacgtgtac cttacgacca     840
```

```
tccagacctt taatccagcg gcgtttccac ttgacttgtt gctcaccagc tacccattga    900
gaggactcga caagtgtctg ttggatagac tcgcggagtg ctgcaatcgc gggggtgttc    960
tcaaggaatt tcttcttgag ttccttaccg cgctctttac cagcaccaac aatctgtcca   1020
atcttctcat caccagcacc atagaggaac ccatagatga acgtcttagc gttatctcgg   1080
gtaggtagtt cagcagctat ctggttctta gtgtggatgt cgccgttaag aatctcgtga   1140
gcgtactcgc cgttatcaaa gcgagccatg aagtgagcca agcagcgtag ctcaagaccg   1200
gatgcgtcga tgccagcctg aacccaaggc ttaccagtta tcccatccaa atggtgctca   1260
gcgccaaaag cagcgcgaca ctgctctcca taaggagaac gtacacccgg aatttgcgca   1320
aggtttggga acgcatgggt cgcacgaccc gtaactgctc cattagggtt aacagaacca   1380
tgaatcttac catcctcagc aacataacga agccatgctt tgtctccctc agcagactgt   1440
ccgattcgct tctgaatcat caagtactct ttaatgaggt cgatagcggc ttgcttctca   1500
gggtcatcta cacgtactcc ttcgagtacc tcatcgtcca ccacaggagc acccttatcg   1560
gtgtacttgg tcgggaccca cccagcctct tggagtttct tctgaatgtg gtcacgagac   1620
gaagggttaa acacaacatg ttcaactggg gtgtaaggag caccagcaac gtactcgcgg   1680
gtatcaagtt cgcaaggctc acggccttct cgctgtgcct tgttcttagg cttcttaaag   1740
ataccaccaa ctttaggtgt cttaatgcga gggtatttag gtagtggctt acctgttcgc   1800
ggatggcaga acatctcagt gccaccttta ggctgatacc acgagccgaa cgtttcggtc   1860
aatttacgga gcaactcaga gcggcgagca gctaactcta cgtacaactc ttcgattgct   1920
tttgtgtcaa acgggaaccc gttgcgctct tgtttagcga gcagccatgc agcacgatgt   1980
tcaatgtcaa cggcctcaag ggattctgac cagaacgtag tgtatcctac gtccgtaaag   2040
tcaatctcag gagggaagta atgtttgtca gagagtagct tctcaaggag agctttagtt   2100
accacaacgt cctgaacgtt atagtccatc atctcttcgt tgaagttcca ccactccatt   2160
ccgtcaacgt attcttcacc ctgctcttca agcattccgg gcaacttgcc ggaacgcaga   2220
agacccatat cggtgtcctt gaggttggaa tgaatcaaac gtgacaacac aagggtgtca   2280
atacagttct cacgaggaag gtggaactct cggttcaatt gcaactttgc cagtttggtc   2340
aatgcaggaa cgtcatactt gtgaccgttg tggaacacaa taagaccgcc tcgtgcaacc   2400
tcggcttcca gcgcatccag atacgcaccg aagtcactcg gacggtagct tacgtactca   2460
gcggtggagt agtcgtagat aaccccgcag tggaacttag tgacgctctc taagagggcg   2520
ttagcttcga tgtcagaaac gatcatatgg ctgccgcgcg gcaccaggcc gctgctgtga   2580
tgatgatgat gatggctgct gcccatggta tatctccttc ttaaagttaa acaaaattat   2640
ttctagaggg aaaccgttgt ggtctcccta tagtgagtcg tattaatttc gcgggatcga   2700
gatctcgatc ctctacgccg gacgcatcgt ggccggcatc accggcgcca caggtgcggt   2760
tgctggcgcc tatatcgccg acatcaccga tggggaagat cgggctcgcc acttcgggct   2820
catgagcgct tgtttcggcg tgggtatggt ggcaggcccc gtggccgggg gactgttggg   2880
cgccatctcc ttgcatgcac cattccttgc ggcggcggtg ctcaacggcc tcaacctact   2940
actgggctgc ttcctaatgc aggagtcgca taagggagag cgtcgaccga tgcccttgag   3000
agccttcaac ccagtcagct ccttccggtg ggcgcggggc atgactatcg tcgccgcact   3060
tatgactgtc ttctttatca tgcaactcgt aggacaggtg ccggcagcgc tctgggtcat   3120
tttcggcgag gaccgctttc gctggagcgc gacgatgatc ggcctgtcgc ttgcggtatt   3180
cggaatcttg cacgccctcg ctcaagcctt cgtcactggt cccgccacca aacgtttcgg   3240
```

```
cgagaagcag gccattatcg ccggcatggc ggccgacgcg ctgggctacg tcttgctggc   3300
gttcgcgacg cgaggctgga tggccttccc cattatgatt cttctcgctt ccggcggcat   3360
cgggatgccc gcgttgcagg ccatgctgtc caggcaggta gatgacgacc atcagggaca   3420
gcttcaagga tcgctcgcgg ctcttaccag cctaacttcg atcactggac cgctgatcgt   3480
cacggcgatt tatgccgcct cggcgagcac atggaacggg ttggcatgga ttgtaggcgc   3540
cgccctatac cttgtctgcc tccccgcgtt gcgtcgcggt gcatggagcc gggccacctc   3600
gacctgaatg gaagccggcg gcacctcgct aacggattca ccactccaag aattggagcc   3660
aatcaattct tgcggagaac tgtgaatgcg caaaccaacc cttggcagaa catatccatc   3720
gcgtccgcca tctccagcag ccgcacgcgg cgcatctcgg gcagcgttgg gtcctggcca   3780
cgggtgcgca tgatcgtgct cctgtcgttg aggacccggc taggctggcg gggttgcctt   3840
actggttagc agaatgaatc accgatacgc gagcgaacgt gaagcgactg ctgctgcaaa   3900
acgtctgcga cctgagcaac aacatgaatg gtcttcggtt tccgtgtttc gtaaagtctg   3960
gaaacgcgga agtcagcgcc ctgcaccatt atgttccgga tctgcatcgc aggatgctgc   4020
tggctaccct gtggaacacc tacatctgta ttaacgaagc gctggcattg accctgagtg   4080
atttttctct ggtcccgccg catccatacc gccagttgtt taccctcaca acgttccagt   4140
aaccgggcat gttcatcatc agtaacccgt atcgtgagca tcctctctcg tttcatcggt   4200
atcattaccc ccatgaacag aaatccccct tacacggagg catcagtgac caaacaggaa   4260
aaaaccgccc ttaacatggc ccgctttatc agaagccaga cattaacgct tctggagaaa   4320
ctcaacgagc tggacgcgga tgaacaggca gacatctgtg aatcgcttca cgaccacgct   4380
gatgagcttt accgcagctg cctcgcgcgt ttcggtgatg acggtgaaaa cctctgacac   4440
atgcagctcc cggagacggt cacagcttgt ctgtaagcgg atgccgggag cagacaagcc   4500
cgtcagggcg cgtcagcggg tgttggcggg tgtcggggcg cagccatgac ccagtcacgt   4560
agcgatagcg gagtgtatac tggcttaact atgcggcatc agagcagatt gtactgagag   4620
tgcaccatat atgcggtgtg aaataccgca cagatgcgta aggagaaaat accgcatcag   4680
gcgctcttcc gcttcctcgc tcactgactc gctgcgctcg gtcgttcggc tgcggcgagc   4740
ggtatcagct cactcaaagg cggtaatacg gttatccaca gaatcagggg ataacgcagg   4800
aaagaacatg tgagcaaaag gccagcaaaa ggccaggaac cgtaaaaagg ccgcgttgct   4860
ggcgtttttc cataggctcc gcccccctga cgagcatcac aaaaatcgac gctcaagtca   4920
gaggtggcga aacccgacag gactataaag ataccaggcg tttccccctg gaagctccct   4980
cgtgcgctct cctgttccga ccctgccgct taccggatac ctgtccgcct ttctcccttc   5040
gggaagcgtg gcgctttctc atagctcacg ctgtaggtat ctcagttcgg tgtaggtcgt   5100
tcgctccaag ctgggctgtg tgcacgaacc ccccgttcag cccgaccgct gcgccttatc   5160
cggtaactat cgtcttgagt ccaacccggt aagacacgac ttatcgccac tggcagcagc   5220
cactggtaac aggattagca gagcgaggta tgtaggcggt gctacagagt tcttgaagtg   5280
gtggcctaac tacggctaca ctagaaggac agtatttggt atctgcgctc tgctgaagcc   5340
agttaccttc ggaaaaagag ttggtagctc ttgatccggc aaacaaacca ccgctggtag   5400
cggtggtttt tttgtttgca agcagcagat tacgcgcaga aaaaaaggat ctcaagaaga   5460
tcctttgatc ttttctacgg ggtctgacgc tcagtggaac gaaaactcac gttaagggat   5520
tttggtcatg agattatcaa aaggatcttc acctagatcc ttttaaatt aaaaatgaag    5580
ttttaaatca atctaaagta tatatgagta aacttggtct gacagttacc aatgcttaat   5640
```

```
cagtgaggca cctatctcag cgatctgtct atttcgttca tccatagttg cctgactccc   5700

cgtcgtgtag ataactacga tacgggaggg cttaccatct ggccccagtg ctgcaatgat   5760

accgcgagac ccacgctcac cggctccaga tttatcagca ataaaccagc cagccggaag   5820

ggccgagcgc agaagtggtc ctgcaacttt atccgcctcc atccagtcta ttaattgttg   5880

ccgggaagct agagtaagta gttcgccagt taatagtttg cgcaacgttg ttgccattgc   5940

tgcaggcatc gtggtgtcac gctcgtcgtt tggtatggct tcattcagct ccggttccca   6000

acgatcaagg cgagttacat gatcccccat gttgtgcaaa aaagcggtta gctccttcgg   6060

tcctccgatc gttgtcagaa gtaagttggc cgcagtgtta tcactcatgg ttatggcagc   6120

actgcataat tctcttactg tcatgccatc cgtaagatgc ttttctgtga ctggtgagta   6180

ctcaaccaag tcattctgag aatagtgtat gcggcgaccg agttgctctt gcccggcgtc   6240

aacacgggat aataccgcgc cacatagcag aactttaaaa gtgctcatca ttggaaaacg   6300

ttcttcgggg cgaaaactct caaggatctt accgctgttg agatccagtt cgatgtaacc   6360

cactcgtgca cccaactgat cttcagcatc ttttactttc accagcgttt ctgggtgagc   6420

aaaaacagga aggcaaaatg ccgcaaaaaa gggaataagg gcgacacgga aatgttgaat   6480

actcatactc ttcctttttc aatattattg aagcatttat cagggttatt gtctcatgag   6540

cggatacata tttgaatgta tttagaaaaa taaacaaata ggggttccgc gcacatttcc   6600

ccgaaaagtg ccacctgacg tctaagaaac cattattatc atgacattaa cctataaaaa   6660

taggcgtatc acgaggccct ttcgtcttca agaa                               6694
```

<210> SEQ ID NO 4
<211> LENGTH: 24
<212> TYPE: DNA
<213> ORGANISM: Artificial
<220> FEATURE:
<223> OTHER INFORMATION: Lys3Cys3 insertion fwd

<400> SEQUENCE: 4

```
tagcaaaaaa aaatgttgct gttc                                            24
```

<210> SEQ ID NO 5
<211> LENGTH: 24
<212> TYPE: DNA
<213> ORGANISM: Artificial
<220> FEATURE:
<223> OTHER INFORMATION: Lys3Cys3 insetion rev

<400> SEQUENCE: 5

```
tagaacagca acattttttt ttgc                                            24
```

<210> SEQ ID NO 6
<211> LENGTH: 6718
<212> TYPE: DNA
<213> ORGANISM: Artificial
<220> FEATURE:
<223> OTHER INFORMATION: plasmid vector, pET-14-C3T7g5(D28)

<400> SEQUENCE: 6

```
ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatatc gtccattccg acagcatcgc cagtcactat ggcgtgctgc tagcgctata    240

tgcgttgatg caatttctat gcgcacccgt tctcggagca ctgtccgacc gctttggccg    300
```

```
ccgcccagtc ctgctcgctt cgctacttgg agccactatc gactacgcga tcatggcgac    360
cacacccgtc ctgtggatat ccggatatag ttcctccttt cagcaaaaaa cccctcaaga    420
cccgtttaga ggccccaagg ggttatgcta gttattgctc agcggtggca gcagccaact    480
cagcttcctt tcgggctttg ttagcagccg gatcctcagt ggcaaatcgc ccaattagga    540
cccatcttac cttcggtatc cagaagacac cggaagttcc agtggtctcc aacccagcgc    600
atcgcttctt gtgcggtctc aatgaccacc tgagcaatct cttcggtacg gcagcctact    660
tggatttcat catgtaccca tgccatgtac gcaaagtccc catcccagcc atgcttcaag    720
cctttctcta cgagcatctc ttcggtcttg ataatccaca gtttgcagat gagagcacca    780
gcagattgca gtagggtatt caaggcagcg tgaggactac gaacgtgtac cttacgacca    840
tccagacctt taatccagcg gcgtttccac ttgacttgtt gctcaccagc tacccattga    900
gaggactcga caagtgtctg ttggatagac tcgcggagtg ctgcaatcgc gggggtgttc    960
tcaaggaatt tcttcttgag ttccttaccg cgctctttac cagcaccaac aatctgtcca   1020
atcttctcat caccagcacc atagaggaac ccatagatga acgtcttagc gttatctcgg   1080
gtaggtagtt cagcagctat ctggttctta gtgtggatgt cgccgttaag aatctcgtga   1140
gcgtactcgc cgttatcaaa gcgagccatg aagtgagcca agcagcgtag ctcaagaccg   1200
gatgcgtcga tgccagcctg aacccaaggc ttaccagtta tcccatccaa atggtgctca   1260
gcgccaaaag cagcgcgaca ctgctctcca taaggagaac gtacacccgg aatttgcgca   1320
aggtttggga acgcatgggt cgcacgaccc gtaactgctc cattagggtt aacagaacca   1380
tgaatcttac catcctcagc aacataacga agccatgctt tgtctccctc agcagactgt   1440
ccgattcgct tctgaatcat caagtactct ttaatgaggt cgatagcggc ttgcttctca   1500
gggtcatcta cacgtactcc ttcgagtacc tcatcgtcca ccacaggagc acccttatcg   1560
gtgtacttgg tcgggaccca cccagcctct tggagtttct tctgaatgtg gtcacgagac   1620
gaagggttaa acacaacatg ttcaactggg gtgtaaggag caccagcaac gtactcgcgg   1680
gtatcaagtt cgcaaggctc acggccttct cgctgtgcct tgttcttagg cttcttaaag   1740
ataccaccaa ctttaggtgt cttaatgcga gggtatttag gtagtggctt acctgttcgc   1800
ggatggcaga acatctcagt gccaccttta ggctgatacc acgagccgaa cgtttcggtc   1860
aatttacgga gcaactcaga gcggcgagca gctaactcta cgtacaactc ttcgattgct   1920
tttgtgtcaa acgggaaccc gttgcgctct tgtttagcga gcagccatgc agcacgatgt   1980
tcaatgtcaa cggcctcaag ggattctgac cagaacgtag tgtatcctac gtccgtaaag   2040
tcaatctcag gagggaagta atgtttgtca gagagtagct tctcaaggag agctttagtt   2100
accacaacgt cctgaacgtt atagtccatc atctcttcgt tgaagttcca ccactccatt   2160
ccgtcaacgt attcttcacc ctgctcttca agcattccgg gcaacttgcc ggaacgcaga   2220
agacccatat cggtgtcctt gaggttggaa tgaatcaaac gtgacaacac aagggtgtca   2280
atacagttct cacgaggaag gtggaactct cggttcaatt gcaactttgc cagtttggtc   2340
aatgcaggaa cgtcatactt gtgaccgttg tggaacacaa taagaccgcc tcgtgcaacc   2400
tcggcttcca gcgcatccag atacgcaccg aagtcactcg gacggtagct tacgtactca   2460
gcggtggagt agtcgtagat aaccccgcag tggaacttag tgacgctctc taagagggcg   2520
ttagcttcga tgtcagaaac gatcatagaa cagcaacatt ttttttgct atggctgccg   2580
cgcggcacca ggccgctgct gtgatgatga tgatgatggc tgctgcccat ggtatatctc   2640
cttcttaaag ttaaacaaaa ttatttctag agggaaaccg ttgtggtctc cctatagtga   2700
```

```
gtcgtattaa tttcgcggga tcgagatctc gatcctctac gccggacgca tcgtggccgg   2760
catcaccggc gccacaggtg cggttgctgg cgcctatatc gccgacatca ccgatgggga   2820
agatcgggct cgccacttcg ggctcatgag cgcttgtttc ggcgtgggta tggtggcagg   2880
ccccgtggcc gggggactgt tgggcgccat ctccttgcat gcaccattcc ttgcggcggc   2940
ggtgctcaac ggcctcaacc tactactggg ctgcttccta atgcaggagt cgcataaggg   3000
agagcgtcga ccgatgccct tgagagcctt caacccagtc agctccttcc ggtgggcgcg   3060
gggcatgact atcgtcgccg cacttatgac tgtcttcttt atcatgcaac tcgtaggaca   3120
ggtgccggca gcgctctggg tcattttcgg cgaggaccgc tttcgctgga gcgcgacgat   3180
gatcggcctg tcgcttgcgg tattcggaat cttgcacgcc ctcgctcaag ccttcgtcac   3240
tggtcccgcc accaaacgtt tcggcgagaa gcaggccatt atcgccggca tggcggccga   3300
cgcgctgggc tacgtcttgc tggcgttcgc gacgcgaggc tggatggcct tccccattat   3360
gattcttctc gcttccggcg gcatcgggat gcccgcgttg caggccatgc tgtccaggca   3420
ggtagatgac gaccatcagg gacagcttca aggatcgctc gcggctctta ccagcctaac   3480
ttcgatcact ggaccgctga tcgtcacggc gatttatgcc gcctcggcga gcacatggaa   3540
cgggttggca tggattgtag gcgccgccct ataccttgtc tgcctccccg cgttgcgtcg   3600
cggtgcatgg agccgggcca cctcgacctg aatggaagcc ggcggcacct cgctaacgga   3660
ttcaccactc caagaattgg agccaatcaa ttcttgcgga gaactgtgaa tgcgcaaacc   3720
aacccttggc agaacatatc catcgcgtcc gccatctcca gcagccgcac gcggcgcatc   3780
tcgggcagcg ttgggtcctg gccacgggtg cgcatgatcg tgctcctgtc gttgaggacc   3840
cggctaggct ggcggggttg ccttactggt tagcagaatg aatcaccgat acgcgagcga   3900
acgtgaagcg actgctgctg caaaacgtct gcgacctgag caacaacatg aatggtcttc   3960
ggtttccgtg tttcgtaaag tctggaaacg cggaagtcag cgccctgcac cattatgttc   4020
cggatctgca tcgcaggatg ctgctggcta ccctgtggaa cacctacatc tgtattaacg   4080
aagcgctggc attgaccctg agtgattttt ctctggtccc gccgcatcca taccgccagt   4140
tgtttaccct cacaacgttc cagtaaccgg gcatgttcat catcagtaac ccgtatcgtg   4200
agcatcctct ctcgtttcat cggtatcatt acccccatga acagaaatcc cccttacacg   4260
gaggcatcag tgaccaaaca ggaaaaaacc gcccttaaca tggcccgctt tatcagaagc   4320
cagacattaa cgcttctgga gaaactcaac gagctggacg cggatgaaca ggcagacatc   4380
tgtgaatcgc ttcacgacca cgctgatgag ctttaccgca gctgcctcgc gcgtttcggt   4440
gatgacggtg aaaacctctg acacatgcag ctcccggaga cggtcacagc ttgtctgtaa   4500
gcggatgccg ggagcagaca agcccgtcag ggcgcgtcag cgggtgttgg cgggtgtcgg   4560
ggcgcagcca tgacccagtc acgtagcgat agcggagtgt atactggctt aactatgcgg   4620
catcagagca gattgtactg agagtgcacc atatatgcgg tgtgaaatac cgcacagatg   4680
cgtaaggaga aaataccgca tcaggcgctc ttccgcttcc tcgctcactg actcgctgcg   4740
ctcggtcgtt cggctgcggc gagcggtatc agctcactca aaggcggtaa tacggttatc   4800
cacagaatca ggggataacg caggaaagaa catgtgagca aaaggccagc aaaaggccag   4860
gaaccgtaaa aaggccgcgt tgctggcgtt tttccatagg ctccgccccc ctgacgagca   4920
tcacaaaaat cgacgctcaa gtcagaggtg gcgaaacccg acaggactat aaagatacca   4980
ggcgtttccc cctggaagct ccctcgtgcg ctctcctgtt ccgaccctgc cgcttaccgg   5040
atacctgtcc gcctttctcc cttcgggaag cgtggcgctt tctcatagct cacgctgtag   5100
```

gtatctcagt tcggtgtagg tcgttcgctc caagctgggc tgtgtgcacg aaccccccgt 5160
tcagcccgac cgctgcgcct tatccggtaa ctatcgtctt gagtccaacc cggtaagaca 5220
cgacttatcg ccactggcag cagccactgg taacaggatt agcagagcga ggtatgtagg 5280
cggtgctaca gagttcttga agtggtggcc taactacggc tacactagaa ggacagtatt 5340
tggtatctgc gctctgctga agccagttac cttcggaaaa agagttggta gctcttgatc 5400
cggcaaacaa accaccgctg gtagcggtgg tttttttgtt tgcaagcagc agattacgcg 5460
cagaaaaaaa ggatctcaag aagatccttt gatcttttct acggggtctg acgctcagtg 5520
gaacgaaaac tcacgttaag ggattttggt catgagatta tcaaaaagga tcttcaccta 5580
gatcctttta aattaaaaat gaagttttaa atcaatctaa agtatatatg agtaaacttg 5640
gtctgacagt taccaatgct taatcagtga ggcacctatc tcagcgatct gtctatttcg 5700
ttcatccata gttgcctgac tccccgtcgt gtagataact acgatacggg agggcttacc 5760
atctggcccc agtgctgcaa tgataccgcg agacccacgc tcaccggctc cagatttatc 5820
agcaataaac cagccagccg gaagggccga gcgcagaagt ggtcctgcaa ctttatccgc 5880
ctccatccag tctattaatt gttgccggga agctagagta agtagttcgc cagttaatag 5940
tttgcgcaac gttgttgcca ttgctgcagg catcgtggtg tcacgctcgt cgtttggtat 6000
ggcttcattc agctccggtt cccaacgatc aaggcgagtt acatgatccc ccatgttgtg 6060
caaaaaagcg gttagctcct tcggtcctcc gatcgttgtc agaagtaagt tggccgcagt 6120
gttatcactc atggttatgg cagcactgca taattctctt actgtcatgc catccgtaag 6180
atgcttttct gtgactggtg agtactcaac caagtcattc tgagaatagt gtatgcggcg 6240
accgagttgc tcttgcccgg cgtcaacacg ggataatacc gcgccacata gcagaacttt 6300
aaaagtgctc atcattggaa aacgttcttc ggggcgaaaa ctctcaagga tcttaccgct 6360
gttgagatcc agttcgatgt aacccactcg tgcacccaac tgatcttcag catcttttac 6420
tttcaccagc gtttctgggt gagcaaaaac aggaaggcaa aatgccgcaa aaaagggaat 6480
aagggcgaca cggaaatgtt gaatactcat actcttcctt tttcaatatt attgaagcat 6540
ttatcagggt tattgtctca tgagcggata catatttgaa tgtatttaga aaaataaaca 6600
aataggggtt ccgcgcacat ttccccgaaa agtgccacct gacgtctaag aaaccattat 6660
tatcatgaca ttaacctata aaaataggcg tatcacgagg ccctttcgtc ttcaagaa 6718

<210> SEQ ID NO 7
<211> LENGTH: 15
<212> TYPE: DNA
<213> ORGANISM: Artificial
<220> FEATURE:
<223> OTHER INFORMATION: molecular wire fwd

<400> SEQUENCE: 7
acagcatcgc cagtc 15

<210> SEQ ID NO 8
<211> LENGTH: 15
<212> TYPE: DNA
<213> ORGANISM: Artificial
<220> FEATURE:
<223> OTHER INFORMATION: molecular wire rev

<400> SEQUENCE: 8
gactggcgat gctgt 15

<210> SEQ ID NO 9
<211> LENGTH: 140
<212> TYPE: DNA
<213> ORGANISM: Artificial
<220> FEATURE:
<223> OTHER INFORMATION: Target DNA model #1

<400> SEQUENCE: 9
aggattataa atcatgctgc tataaagaca catgcacacg catgtttatt acagcactat 60
tcacgatagc aaagacttgg aaccaaccca aatgtccaac aatgatagac tggattaaga 120
aaatgtggca catatacacc 140

<210> SEQ ID NO 10
<211> LENGTH: 25
<212> TYPE: DNA
<213> ORGANISM: Artificial
<220> FEATURE:
<223> OTHER INFORMATION: Primer

<400> SEQUENCE: 10
gccacatttt cttaatccag tctat 25

<210> SEQ ID NO 11
<211> LENGTH: 13
<212> TYPE: PRT
<213> ORGANISM: Artificial
<220> FEATURE:
<223> OTHER INFORMATION: motif 1

<400> SEQUENCE: 11

Asp Tyr Ser Gln Ile Glu Leu Arg Val Leu Ala His Leu
1 5 10

<210> SEQ ID NO 12
<211> LENGTH: 10
<212> TYPE: PRT
<213> ORGANISM: Artificial
<220> FEATURE:
<223> OTHER INFORMATION: motif 2

<400> SEQUENCE: 12

Arg Met Leu Leu Gln Val His Asp Glu Leu
1 5 10

<210> SEQ ID NO 13
<211> LENGTH: 45
<212> TYPE: DNA
<213> ORGANISM: Artificial
<220> FEATURE:
<223> OTHER INFORMATION: PCR primer

<400> SEQUENCE: 13
aataatccat ggccctggag gaggccccct ggcccccgcc ggaag 45

<210> SEQ ID NO 14
<211> LENGTH: 45
<212> TYPE: DNA
<213> ORGANISM: Artificial
<220> FEATURE:
<223> OTHER INFORMATION: PCR primer

<400> SEQUENCE: 14
aataatgtcg actcactcct tggcggagag ccagtcctcc cctat 45

<210> SEQ ID NO 15
<211> LENGTH: 541

```
<212> TYPE: PRT
<213> ORGANISM: Thermus aquaticus
<220> FEATURE:
<221> NAME/KEY: Stoffel fragment of DNA polymerase
<222> LOCATION: (1)..(541)

<400> SEQUENCE: 15

Met Ala Leu Glu Glu Ala Pro Trp Pro Pro Pro Glu Gly Ala Phe Val
1               5                   10                  15

Gly Phe Val Leu Ser Arg Lys Glu Pro Met Trp Ala Asp Leu Leu Ala
            20                  25                  30

Leu Ala Ala Ala Arg Gly Gly Arg Val His Arg Ala Pro Glu Pro Tyr
        35                  40                  45

Lys Ala Leu Arg Asp Leu Lys Glu Ala Arg Gly Leu Leu Ala Lys Asp
    50                  55                  60

Leu Ser Val Leu Ala Leu Arg Glu Gly Leu Gly Leu Pro Pro Gly Asp
65                  70                  75                  80

Asp Pro Met Leu Leu Ala Tyr Leu Leu Asp Pro Ser Asn Thr Thr Pro
                85                  90                  95

Glu Gly Val Ala Arg Arg Tyr Gly Gly Glu Trp Thr Glu Glu Ala Gly
            100                 105                 110

Glu Arg Ala Ala Leu Ser Glu Arg Leu Phe Ala Asn Leu Trp Gly Arg
        115                 120                 125

Leu Glu Gly Glu Glu Arg Leu Leu Trp Leu Tyr Arg Glu Val Glu Arg
    130                 135                 140

Pro Leu Ser Ala Val Leu Ala His Met Glu Ala Thr Gly Val Arg Leu
145                 150                 155                 160

Asp Val Ala Tyr Leu Arg Ala Leu Ser Leu Glu Val Ala Glu Glu Ile
                165                 170                 175

Ala Arg Leu Glu Ala Glu Val Phe Arg Leu Ala Gly His Pro Phe Asn
            180                 185                 190

Leu Asn Ser Arg Asp Gln Leu Glu Arg Val Leu Phe Asp Glu Leu Gly
        195                 200                 205

Leu Pro Ala Ile Gly Lys Thr Glu Lys Thr Gly Lys Arg Ser Thr Ser
    210                 215                 220

Ala Ala Val Leu Glu Ala Leu Arg Glu Ala His Pro Ile Val Glu Lys
225                 230                 235                 240

Ile Leu Gln Tyr Arg Glu Leu Thr Lys Leu Lys Ser Thr Tyr Ile Asp
                245                 250                 255

Pro Leu Pro Asp Leu Ile His Pro Arg Thr Gly Arg Leu His Thr Arg
            260                 265                 270

Phe Asn Gln Thr Ala Thr Ala Thr Gly Arg Leu Ser Ser Ser Asp Pro
        275                 280                 285

Asn Leu Gln Asn Ile Pro Val Arg Thr Pro Leu Gly Gln Arg Ile Arg
    290                 295                 300

Arg Ala Phe Ile Ala Glu Glu Gly Trp Leu Leu Val Ala Leu Asp Tyr
305                 310                 315                 320

Ser Gln Ile Glu Leu Arg Val Leu Ala His Leu Ser Gly Asp Glu Asn
                325                 330                 335

Leu Ile Arg Val Phe Gln Glu Gly Arg Asp Ile His Thr Glu Thr Ala
            340                 345                 350

Ser Trp Met Phe Gly Val Pro Arg Glu Ala Val Asp Pro Leu Met Arg
        355                 360                 365

Arg Ala Ala Lys Thr Ile Asn Phe Gly Val Leu Tyr Gly Met Ser Ala
    370                 375                 380
```

```
His Arg Leu Ser Gln Glu Leu Ala Ile Pro Tyr Glu Glu Ala Gln Ala
385                 390                 395                 400

Phe Ile Glu Arg Tyr Phe Gln Ser Phe Pro Lys Val Arg Ala Trp Ile
                405                 410                 415

Glu Lys Thr Leu Glu Glu Gly Arg Arg Arg Gly Tyr Val Glu Thr Leu
            420                 425                 430

Phe Gly Arg Arg Arg Tyr Val Pro Asp Leu Glu Ala Arg Val Lys Ser
        435                 440                 445

Val Arg Glu Ala Ala Glu Arg Met Ala Phe Asn Met Pro Val Gln Gly
    450                 455                 460

Thr Ala Ala Asp Leu Met Lys Leu Ala Met Val Lys Leu Phe Pro Arg
465                 470                 475                 480

Leu Glu Glu Met Gly Ala Arg Met Leu Leu Gln Val His Asp Glu Leu
                485                 490                 495

Val Leu Glu Ala Pro Lys Glu Arg Ala Glu Ala Val Ala Arg Leu Ala
            500                 505                 510

Lys Glu Val Met Glu Gly Val Tyr Pro Leu Ala Val Pro Leu Glu Val
        515                 520                 525

Glu Val Gly Ile Gly Glu Asp Trp Leu Ser Ala Lys Glu
    530                 535                 540
```

<210> SEQ ID NO 16
<211> LENGTH: 6784
<212> TYPE: DNA
<213> ORGANISM: Artificial
<220> FEATURE:
<223> OTHER INFORMATION: plasmid pET-TaqDP

<400> SEQUENCE: 16

```
ggggaattgt gagcggataa caattcccct ctagaaataa ttttgtttaa ctttaagaag     60

gagatatacc atggccctgg aggaggcccc ctggcccccg ccggaagggg ccttcgtggg    120

ctttgtgctt tcccgcaagg agcccatgtg ggccgatctt ctggccctgg ccgccgccag    180

ggggggccgg gtccaccggg cccccgagcc ttataaagcc ctcagggacc tgaaggaggc    240

gcgggggctt ctcgccaaag acctgagcgt tctggccctg agggaaggcc ttggcctccc    300

gcccggcgac gaccccatgc tcctcgccta cctcctggac ccttccaaca ccacccccga    360

gggggtggcc cggcgctacg gcggggagtg gacggaggag gcgggggagc gggccgccct    420

ttccgagagg ctcttcgcca acctgtgggg gaggcttgag ggggaggaga ggctcctttg    480

gctttaccgg gaggtggaga ggcccctttc cgctgtcctg gcccacatgg aggccacggg    540

ggtgcgcctg gacgtggcct atctcagggc cttgtccctg gaggtggccg aggagatcgc    600

ccgcctcgag gccgaggtct tccgcctggc cggccacccc ttcaacctca actcccggga    660

ccagctggaa agggtcctct ttgacgagct agggcttccc gccatcggca agacggagaa    720

gaccggcaag cgctccacca gcgccgccgt cctggaggcc ctccgcgagg cccaccccat    780

cgtggagaag atcctgcagt accgggagct caccaagctg aagagcacct acattgaccc    840

cttgccggac ctcatccacc ccaggacggg ccgcctccac acccgcttca accagacggc    900

cacggccacg ggcaggctaa gtagctccga tcccaacctc cagaacatcc ccgtccgcac    960

cccgcttggg cagaggatcc gccgggcctt catcgccgag gaggggtggc tattggtggc   1020

cctggactat agccagatag agctcagggt gctggcccac ctctccggcg acgagaacct   1080

gatccgggtc ttccaggagg ggcgggacat ccacacggag accgccagct ggatgttcgg   1140

cgtccccccgg gaggccgtgg accccctgat gcgccgggcg gccaagacca tcaacttcgg   1200
```

```
ggtcctctac ggcatgtcgg cccaccgcct ctcccaggag ctagccatcc cttacgagga   1260
ggcccaggcc ttcattgagc gctactttca gagcttcccc aaggtgcggg cctggattga   1320
gaagaccctg gaggagggca ggaggcgggg gtacgtggag accctcttcg gccgccgccg   1380
ctacgtgcca gacctagagg cccgggtgaa gagcgtgcgg gaggcggccg agcgcatggc   1440
cttcaacatg cccgtccagg gcaccgccgc cgacctcatg aagctggcta tggtgaagct   1500
cttccccagg ctggaggaaa tgggggccag gatgctcctt caggtccacg acgagctggt   1560
cctcgaggcc ccaaaagaga gggcggaggc cgtggcccgg ctggccaagg aggtcatgga   1620
gggggtgtat cccctggccg tgcccctgga ggtggaggtg gggataggg aggactggct    1680
ctccgccaag gagtgagtcg acaagcttgc ggccgcactc gagtctggta aagaaaccgc   1740
tgctgcgaaa tttgaacgcc agcacatgga ctcgtctact agcgcagctt aattaaccta   1800
ggctgctgcc accgctgagc aataactagc ataacccctt ggggcctcta aacgggtctt   1860
gaggggtttt ttgctgaaag gaggaactat atccggattg gcgaatggga cgcgccctgt   1920
agcggcgcat taagcgcggc gggtgtggtg gttacgcgca gcgtgaccgc tacacttgcc   1980
agcgccctag cgcccgctcc tttcgctttc ttcccttcct ttctcgccac gttcgccggc   2040
tttccccgtc aagctctaaa tcgggggctc cctttagggt tccgatttag tgctttacgg   2100
cacctcgacc ccaaaaaact tgattagggt gatggttcac gtagtgggcc atcgccctga   2160
tagacggttt ttcgcccttt gacgttggag tccacgttct ttaatagtgg actcttgttc   2220
caaactggaa caacactcaa ccctatctcg gtctattctt ttgatttata agggattttg   2280
ccgatttcgg cctattggtt aaaaaatgag ctgatttaac aaaaatttaa cgcgaatttt   2340
aacaaaatat taacgtttac aatttctggc ggcacgatgg catgagatta tcaaaaagga   2400
tcttcaccta gatcctttta aattaaaaat gaagttttaa atcaatctaa agtatatatg   2460
agtaaacttg gtctgacagt taccaatgct taatcagtga ggcacctatc tcagcgatct   2520
gtctatttcg ttcatccata gttgcctgac tccccgtcgt gtagataact acgatacggg   2580
agggcttacc atctggcccc agtgctgcaa tgataccgcg agacccacgc tcaccggctc   2640
cagatttatc agcaataaac cagccagccg gaagggccga gcgcagaagt ggtcctgcaa   2700
ctttatccgc ctccatccag tctattaatt gttgccggga agctagagta agtagttcgc   2760
cagttaatag tttgcgcaac gttgttgcca ttgctacagg catcgtggtg tcacgctcgt   2820
cgtttggtat ggcttcattc agctccggtt cccaacgatc aaggcgagtt acatgatccc   2880
ccatgttgtg caaaaaagcg gttagctcct tcggtcctcc gatcgttgtc agaagtaagt   2940
tggccgcagt gttatcactc atggttatgg cagcactgca taattctctt actgtcatgc   3000
catccgtaag atgcttttct gtgactggtg agtactcaac caagtcattc tgagaatagt   3060
gtatgcggcg accgagttgc tcttgcccgg cgtcaatacg ggataatacc gcgccacata   3120
gcagaacttt aaaagtgctc atcattggaa aacgttcttc ggggcgaaaa ctctcaagga   3180
tcttaccgct gttgagatcc agttcgatgt aacccactcg tgcacccaac tgatcttcag   3240
catcttttac tttcaccagc gtttctgggt gagcaaaaac aggaaggcaa aatgccgcaa   3300
aaaagggaat aagggcgaca cggaaatgtt gaatactcat actcttcctt tttcaatcat   3360
gattgaagca tttatcaggg ttattgtctc atgagcggat acatatttga atgtatttag   3420
aaaaataaac aaataggtca tgaccaaaat cccttaacgt gagttttcgt tccactgagc   3480
gtcagacccc gtagaaaaga tcaaaggatc ttcttgagat cctttttttc tgcgcgtaat   3540
ctgctgcttg caaacaaaaa aaccaccgct accagcggtg gtttgtttgc cggatcaaga   3600
```

-continued

```
gctaccaact ctttttccga aggtaactgg cttcagcaga gcgcagatac caaatactgt   3660
ccttctagtg tagccgtagt taggccacca cttcaagaac tctgtagcac cgcctacata   3720
cctcgctctg ctaatcctgt taccagtggc tgctgccagt ggcgataagt cgtgtcttac   3780
cgggttggac tcaagacgat agttaccgga taaggcgcag cggtcgggct gaacgggggg   3840
ttcgtgcaca cagcccagct tggagcgaac gacctacacc gaactgagat acctacagcg   3900
tgagctatga gaaagcgcca cgcttcccga agggagaaag gcggacaggt atccggtaag   3960
cggcagggtc ggaacaggag agcgcacgag ggagcttcca gggggaaacg cctggtatct   4020
ttatagtcct gtcgggtttc gccacctctg acttgagcgt cgatttttgt gatgctcgtc   4080
aggggggcgg agcctatgga aaaacgccag caacgcggcc tttttacggt tcctggcctt   4140
ttgctggcct tttgctcaca tgttctttcc tgcgttatcc cctgattctg tggataaccg   4200
tattaccgcc tttgagtgag ctgataccgc tcgccgcagc cgaacgaccg agcgcagcga   4260
gtcagtgagc gaggaagcgg aagagcgcct gatgcggtat tttctcctta cgcatctgtg   4320
cggtatttca caccgcatat atggtgcact ctcagtacaa tctgctctga tgccgcatag   4380
ttaagccagt atacactccg ctatcgctac gtgactgggt catggctgcg ccccgacacc   4440
cgccaacacc cgctgacgcg ccctgacggg cttgtctgct cccggcatcc gcttacagac   4500
aagctgtgac cgtctccggg agctgcatgt gtcagaggtt ttcaccgtca tcaccgaaac   4560
gcgcgaggca gctgcggtaa agctcatcag cgtggtcgtg aagcgattca cagatgtctg   4620
cctgttcatc cgcgtccagc tcgttgagtt tctccagaag cgttaatgtc tggcttctga   4680
taaagcgggc catgttaagg gcggtttttt cctgtttggt cactgatgcc tccgtgtaag   4740
ggggatttct gttcatgggg gtaatgatac cgatgaaacg agagaggatg ctcacgatac   4800
gggttactga tgatgaacat gcccggttac tggaacgttg tgagggtaaa caactggcgg   4860
tatggatgcg gcgggaccag agaaaaatca ctcagggtca atgccagcgc ttcgttaata   4920
cagatgtagg tgttccacag ggtagccagc agcatcctgc gatgcagatc cggaacataa   4980
tggtgcaggg cgctgacttc cgcgtttcca gactttacga aacacggaaa ccgaagacca   5040
ttcatgttgt tgctcaggtc gcagacgttt tgcagcagca gtcgcttcac gttcgctcgc   5100
gtatcggtga ttcattctgc taaccagtaa ggcaaccccg ccagcctagc cgggtcctca   5160
acgacaggag cacgatcatg ctagtcatgc cccgcgccca ccggaaggag ctgactgggt   5220
tgaaggctct caagggcatc ggtcgagatc ccggtgccta atgagtgagc taacttacat   5280
taattgcgtt gcgctcactg cccgctttcc agtcgggaaa cctgtcgtgc cagctgcatt   5340
aatgaatcgg ccaacgcgcg gggagaggcg gtttgcgtat tgggcgccag ggtggttttt   5400
cttttcacca gtgagacggg caacagctga ttgcccttca ccgcctggcc ctgagagagt   5460
tgcagcaagc ggtccacgct ggtttgcccc agcaggcgaa aatcctgttt gatggtggtt   5520
aacggcggga tataacatga gctgtcttcg gtatcgtcgt atcccactac cgagatgtcc   5580
gcaccaacgc gcagcccgga ctcggtaatg gcgcgcattg cgcccagcgc catctgatcg   5640
ttggcaacca gcatcgcagt gggaacgatg ccctcattca gcatttgcat ggtttgttga   5700
aaaccggaca tggcactcca gtcgccttcc cgttccgcta tcggctgaat ttgattgcga   5760
gtgagatatt tatgccagcc agccagacgc agacgcgccg agacagaact taatgggccc   5820
gctaacagcg cgatttgctg gtgacccaat gcgaccagat gctccacgcc cagtcgcgta   5880
ccgtcttcat gggagaaaat aatactgttg atgggtgtct ggtcagagac atcaagaaat   5940
aacgccggaa cattagtgca ggcagcttcc acagcaatgg catcctggtc atccagcgga   6000
```

```
tagttaatga tcagcccact gacgcgttgc gcgagaagat tgtgcaccgc cgctttacag   6060

gcttcgacgc cgcttcgttc taccatcgac accaccacgc tggcacccag ttgatcggcg   6120

cgagatttaa tcgccgcgac aatttgcgac ggcgcgtgca gggccagact ggaggtggca   6180

acgccaatca gcaacgactg tttgcccgcc agttgttgtg ccacgcggtt gggaatgtaa   6240

ttcagctccg ccatcgccgc ttccactttt tcccgcgttt tcgcagaaac gtggctggcc   6300

tggttcacca cgcgggaaac ggtctgataa gagacaccgg catactctgc gacatcgtat   6360

aacgttactg gtttcacatt caccaccctg aattgactct cttccgggcg ctatcatgcc   6420

ataccgcgaa aggttttgcg ccattcgatg gtgtccggga tctcgacgct ctcccttatg   6480

cgactcctgc attaggaagc agcccagtag taggttgagg ccgttgagca ccgccgccgc   6540

aaggaatggt gcatgcaagg agatggcgcc caacagtccc ccggccacgg ggcctgccac   6600

catacccacg ccgaaacaag cgctcatgag cccgaagtgg cgagcccgat cttccccatc   6660

ggtgatgtcg gcgatatagg cgccagcaac cgcacctgtg gcgccggtga tgccggccac   6720

gatgcgtccg gcgtagagga tcgagatcga tctcgatccc gcgaaattaa tacgactcac   6780

tata                                                                6784
```

```
<210> SEQ ID NO 17
<211> LENGTH: 541
<212> TYPE: PRT
<213> ORGANISM: Artificial
<220> FEATURE:
<223> OTHER INFORMATION: DNA polymerase

<400> SEQUENCE: 17

Met Ala Leu Glu Glu Ala Pro Trp Pro Pro Pro Glu Gly Ala Phe Val
1               5                   10                  15

Gly Phe Val Leu Ser Arg Lys Glu Pro Met Trp Ala Asp Leu Leu Ala
            20                  25                  30

Leu Ala Ala Ala Arg Gly Gly Arg Val His Arg Ala Pro Glu Pro Tyr
        35                  40                  45

Lys Ala Leu Arg Asp Leu Lys Glu Ala Arg Gly Leu Leu Ala Lys Asp
    50                  55                  60

Leu Ser Val Leu Ala Leu Arg Glu Gly Leu Gly Leu Pro Pro Gly Asp
65                  70                  75                  80

Asp Pro Met Leu Leu Ala Tyr Leu Leu Asp Pro Ser Asn Thr Thr Pro
                85                  90                  95

Glu Gly Val Ala Arg Arg Tyr Gly Gly Glu Trp Thr Glu Glu Ala Gly
            100                 105                 110

Glu Arg Ala Ala Leu Ser Glu Arg Leu Phe Ala Asn Leu Trp Gly Arg
        115                 120                 125

Leu Glu Gly Glu Glu Arg Leu Leu Trp Leu Tyr Arg Glu Val Glu Arg
    130                 135                 140

Pro Leu Ser Ala Val Leu Ala His Met Glu Ala Thr Gly Val Arg Leu
145                 150                 155                 160

Asp Val Ala Tyr Leu Arg Ala Leu Ser Leu Glu Val Ala Glu Glu Ile
                165                 170                 175

Ala Arg Leu Glu Ala Glu Val Phe Arg Leu Ala Gly His Pro Phe Asn
            180                 185                 190

Leu Asn Ser Arg Asp Gln Leu Glu Arg Val Leu Phe Asp Glu Leu Gly
        195                 200                 205

Leu Pro Ala Ile Gly Lys Thr Glu Lys Thr Gly Lys Arg Ser Thr Ser
    210                 215                 220
```

```
Ala Ala Val Leu Glu Ala Leu Arg Glu Ala His Pro Ile Val Glu Lys
225                 230                 235                 240

Ile Leu Gln Tyr Arg Glu Leu Thr Lys Leu Lys Ser Thr Tyr Ile Asp
                245                 250                 255

Pro Leu Pro Asp Leu Ile His Pro Arg Thr Gly Arg Leu His Thr Arg
            260                 265                 270

Phe Asn Gln Thr Ala Thr Ala Thr Gly Arg Leu Ser Ser Ser Asp Pro
        275                 280                 285

Asn Leu Gln Asn Ile Pro Val His Thr Pro Leu Gly Gln Arg Ile Arg
    290                 295                 300

Arg Ala Phe Ile Ala Glu Glu Gly Trp Leu Leu Val Ala Leu Asp Tyr
305                 310                 315                 320

Ser His Ile Glu Leu Arg Val Leu Ala His Leu Ser Gly Asp Glu Asn
                325                 330                 335

Leu Ile Arg Val Phe Gln Glu Gly Arg Asp Ile His Thr Glu Thr Ala
            340                 345                 350

Ser Trp Met Phe Gly Val Pro Arg Glu Ala Val Asp Pro Leu Met Arg
        355                 360                 365

Arg Ala Ala Lys Thr Ile Asn His Gly Val Leu Tyr Gly Met Ser Ala
    370                 375                 380

His Arg Leu Ser Gln Glu Leu Ala Ile Pro Tyr Glu Glu Ala Gln Ala
385                 390                 395                 400

Phe Ile Glu Arg Tyr Phe Gln Ser Phe Pro Lys Val Arg Ala Trp Ile
                405                 410                 415

Glu Lys Thr Leu Glu Glu Gly Arg Arg Arg Gly Tyr Val Glu Thr Leu
            420                 425                 430

Phe Gly Arg Arg Arg Tyr Val Pro Asp Leu Glu Ala Arg Val Lys Ser
        435                 440                 445

Val Arg Glu Ala Ala Glu Arg Met Ala Phe Asn Met Pro Val Gln Gly
    450                 455                 460

Thr Ala Ala Asp Leu Met Lys Leu Ala Met Val Lys Leu Phe Pro Arg
465                 470                 475                 480

Leu Glu Glu Met Gly Ala Arg Met Leu Leu Gln Val His Asp Glu Leu
                485                 490                 495

Val Leu Glu Ala Pro Lys Glu Arg Ala Glu Ala Val Ala Arg Leu Ala
            500                 505                 510

Lys Glu Val Met Glu Gly Val Tyr Pro Leu Ala Val Pro Leu Glu Val
        515                 520                 525

Glu Val Gly Ile Gly Glu Asp Trp Leu Ser Ala Lys Glu
    530                 535                 540
```

<210> SEQ ID NO 18
<211> LENGTH: 6784
<212> TYPE: DNA
<213> ORGANISM: Artificial
<220> FEATURE:
<223> OTHER INFORMATION: plasmid pET-mTaqDP

<400> SEQUENCE: 18

```
ggggaattgt gagcggataa caattcccct ctagaaataa ttttgtttaa ctttaagaag     60

gagatatacc atggccctgg aggaggcccc ctggcccccg ccggaagggg ccttcgtggg    120

ctttgtgctt tcccgcaagg agcccatgtg ggccgatctt ctggccctgg ccgccgccag    180

ggggggccgg gtccaccggg cccccgagcc ttataaagcc ctcagggacc tgaaggaggc    240

gcgggggctt ctcgccaaag acctgagcgt tctggccctg agggaaggcc ttggcctccc    300
```

```
gcccggcgac gaccccatgc tcctcgccta cctcctggac ccttccaaca ccaccccga     360
gggggtggcc cggcgctacg gcggggagtg gacggaggag gcgggggagc gggccgccct    420
ttccgagagg ctcttcgcca acctgtgggg gaggcttgag gggaggaga ggctcctttg     480
gctttaccgg gaggtggaga ggcccctttc cgctgtcctg gcccacatgg aggccacggg    540
ggtgcgcctg gacgtggcct atctcagggc cttgtccctg gaggtggccg aggagatcgc    600
ccgcctcgag gccgaggtct tccgcctggc cggccacccc ttcaacctca actcccggga    660
ccagctggaa agggtcctct ttgacgagct agggcttccc gccatcggca agacggagaa    720
gaccggcaag cgctccacca gcgccgccgt cctggaggcc ctccgcgagg cccaccccat    780
cgtggagaag atcctgcagt accgggagct caccaagctg aagagcacct acattgaccc    840
cttgccggac ctcatccacc ccaggacggg ccgcctccac acccgcttca accagacggc    900
cacggccacg ggcaggctaa gtagctccga tcccaacctc cagaacatcc ccgtccatac    960
cccgcttggg cagaggatcc gccgggcctt catcgccgag gaggggtggc tattggtggc   1020
cctggactat agccatatag agctcagggt gctggcccac ctctccggcg acgagaacct   1080
gatccgggtc ttccaggagg ggcgggacat ccacacggag accgccagct ggatgttcgg   1140
cgtcccccgg gaggccgtgg acccctgat gcgccgggcg gccaagacca tcaaccatgg    1200
ggtcctctac ggcatgtcgg cccaccgcct ctcccaggag ctagccatcc cttacgagga   1260
ggcccaggcc ttcattgagc gctactttca gagcttcccc aaggtgcggg cctggattga   1320
gaagaccctg gaggagggca ggaggcgggg gtacgtggag accctcttcg gccgccgccg   1380
ctacgtgcca gacctagagg cccgggtgaa gagcgtgcgg gaggcggccg agcgcatggc   1440
cttcaacatg cccgtccagg gcaccgccgc cgacctcatg aagctggcta tggtgaagct   1500
cttccccagg ctggaggaaa tgggggccag gatgctcctt caggtccacg acgagctggt   1560
cctcgaggcc ccaaaagaga gggcggaggc cgtggcccgg ctggccaagg aggtcatgga   1620
gggggtgtat cccctggccg tgcccctgga ggtggaggtg gggataggg aggactggct    1680
ctccgccaag gagtgagtcg acaagcttgc ggccgcactc gagtctggta aagaaaccgc   1740
tgctgcgaaa tttgaacgcc agcacatgga ctcgtctact agcgcagctt aattaaccta   1800
ggctgctgcc accgctgagc aataactagc ataacccctt ggggcctcta aacgggtctt   1860
gaggggtttt ttgctgaaag gaggaactat atccggattg gcgaatggga cgcgccctgt   1920
agcggcgcat taagcgcggc gggtgtggtg gttacgcgca gcgtgaccgc tacacttgcc   1980
agcgccctag cgcccgctcc tttcgctttc ttcccttcct ttctcgccac gttcgccggc   2040
tttccccgtc aagctctaaa tcgggggctc cctttagggt tccgatttag tgctttacgg   2100
cacctcgacc ccaaaaaact tgattagggt gatggttcac gtagtgggcc atcgccctga   2160
tagacggttt ttcgcccttt gacgttggag tccacgttct ttaatagtgg actcttgttc   2220
caaactggaa caacactcaa ccctatctcg gtctattctt ttgatttata agggattttg   2280
ccgatttcgg cctattggtt aaaaaatgag ctgatttaac aaaaatttaa cgcgaatttt   2340
aacaaaatat taacgtttac aatttctggc ggcacgatgg catgagatta tcaaaaagga   2400
tcttcaccta gatcctttta aattaaaaat gaagttttaa atcaatctaa agtatatatg   2460
agtaaacttg gtctgacagt taccaatgct taatcagtga ggcacctatc tcagcgatct   2520
gtctatttcg ttcatccata gttgcctgac tccccgtcgt gtagataact acgatacggg   2580
agggcttacc atctggcccc agtgctgcaa tgataccgcg agacccacgc tcaccggctc   2640
cagatttatc agcaataaac cagccagccg gaagggccga gcgcagaagt ggtcctgcaa   2700
```

-continued

```
ctttatccgc ctccatccag tctattaatt gttgccggga agctagagta agtagttcgc   2760
cagttaatag tttgcgcaac gttgttgcca ttgctacagg catcgtggtg tcacgctcgt   2820
cgtttggtat ggcttcattc agctccggtt cccaacgatc aaggcgagtt acatgatccc   2880
ccatgttgtg caaaaaagcg gttagctcct tcggtcctcc gatcgttgtc agaagtaagt   2940
tggccgcagt gttatcactc atggttatgg cagcactgca taattctctt actgtcatgc   3000
catccgtaag atgcttttct gtgactggtg agtactcaac caagtcattc tgagaatagt   3060
gtatgcggcg accgagttgc tcttgcccgg cgtcaatacg ggataatacc gcgccacata   3120
gcagaacttt aaaagtgctc atcattggaa aacgttcttc ggggcgaaaa ctctcaagga   3180
tcttaccgct gttgagatcc agttcgatgt aacccactcg tgcacccaac tgatcttcag   3240
catcttttac tttcaccagc gtttctgggt gagcaaaaac aggaaggcaa aatgccgcaa   3300
aaaagggaat aagggcgaca cggaaatgtt gaatactcat actcttcctt tttcaatcat   3360
gattgaagca tttatcaggg ttattgtctc atgagcggat acatatttga atgtatttag   3420
aaaaataaac aaataggtca tgaccaaaat cccttaacgt gagttttcgt tccactgagc   3480
gtcagacccc gtagaaaaga tcaaaggatc ttcttgagat cctttttttc tgcgcgtaat   3540
ctgctgcttg caaacaaaaa aaccaccgct accagcggtg gtttgtttgc cggatcaaga   3600
gctaccaact ctttttccga aggtaactgg cttcagcaga gcgcagatac caaatactgt   3660
ccttctagtg tagccgtagt taggccacca cttcaagaac tctgtagcac cgcctacata   3720
cctcgctctg ctaatcctgt taccagtggc tgctgccagt ggcgataagt cgtgtcttac   3780
cgggttggac tcaagacgat agttaccgga taaggcgcag cggtcgggct gaacgggggg   3840
ttcgtgcaca cagcccagct tggagcgaac gacctacacc gaactgagat acctacagcg   3900
tgagctatga gaaagcgcca cgcttcccga agggagaaag gcggacaggt atccggtaag   3960
cggcagggtc ggaacaggag agcgcacgag ggagcttcca gggggaaacg cctggtatct   4020
ttatagtcct gtcgggtttc gccacctctg acttgagcgt cgatttttgt gatgctcgtc   4080
aggggggcgg agcctatgga aaaacgccag caacgcggcc tttttacggt tcctggcctt   4140
ttgctggcct tttgctcaca tgttctttcc tgcgttatcc cctgattctg tggataaccg   4200
tattaccgcc tttgagtgag ctgataccgc tcgccgcagc cgaacgaccg agcgcagcga   4260
gtcagtgagc gaggaagcgg aagagcgcct gatgcggtat tttctcctta cgcatctgtg   4320
cggtatttca caccgcatat atggtgcact ctcagtacaa tctgctctga tgccgcatag   4380
ttaagccagt atacactccg ctatcgctac gtgactgggt catggctgcg ccccgacacc   4440
cgccaacacc cgctgacgcg ccctgacggg cttgtctgct cccggcatcc gcttacagac   4500
aagctgtgac cgtctccggg agctgcatgt gtcagaggtt ttcaccgtca tcaccgaaac   4560
gcgcgaggca gctgcggtaa agctcatcag cgtggtcgtg aagcgattca cagatgtctg   4620
cctgttcatc cgcgtccagc tcgttgagtt tctccagaag cgttaatgtc tggcttctga   4680
taaagcgggc catgttaagg gcggtttttt cctgtttggt cactgatgcc tccgtgtaag   4740
ggggatttct gttcatgggg gtaatgatac cgatgaaacg agagaggatg ctcacgatac   4800
gggttactga tgatgaacat gcccggttac tggaacgttg tgagggtaaa caactggcgg   4860
tatggatgcg gcgggaccag agaaaaatca ctcagggtca atgccagcgc ttcgttaata   4920
cagatgtagg tgttccacag ggtagccagc agcatcctgc gatgcagatc cggaacataa   4980
tggtgcaggg cgctgacttc cgcgtttcca gactttacga aacacggaaa ccgaagacca   5040
ttcatgttgt tgctcaggtc gcagacgttt tgcagcagca gtcgcttcac gttcgctcgc   5100
```

-continued

```
gtatcggtga ttcattctgc taaccagtaa ggcaaccccg ccagcctagc cgggtcctca   5160

acgacaggag cacgatcatg ctagtcatgc cccgcgccca ccggaaggag ctgactgggt   5220

tgaaggctct caagggcatc ggtcgagatc ccggtgccta atgagtgagc taacttacat   5280

taattgcgtt gcgctcactg cccgctttcc agtcgggaaa cctgtcgtgc cagctgcatt   5340

aatgaatcgg ccaacgcgcg gggagaggcg gtttgcgtat tgggcgccag ggtggttttt   5400

cttttcacca gtgagacggg caacagctga ttgcccttca ccgcctggcc ctgagagagt   5460

tgcagcaagc ggtccacgct ggtttgcccc agcaggcgaa aatcctgttt gatggtggtt   5520

aacggcggga tataacatga gctgtcttcg gtatcgtcgt atcccactac cgagatgtcc   5580

gcaccaacgc gcagcccgga ctcggtaatg gcgcgcattg cgcccagcgc catctgatcg   5640

ttggcaacca gcatcgcagt gggaacgatg ccctcattca gcatttgcat ggtttgttga   5700

aaaccggaca tggcactcca gtcgccttcc cgttccgcta tcggctgaat ttgattgcga   5760

gtgagatatt tatgccagcc agccagacgc agacgcgccg agacagaact taatgggccc   5820

gctaacagcg cgatttgctg gtgacccaat gcgaccagat gctccacgcc cagtcgcgta   5880

ccgtcttcat gggagaaaat aatactgttg atgggtgtct ggtcagagac atcaagaaat   5940

aacgccggaa cattagtgca ggcagcttcc acagcaatgg catcctggtc atccagcgga   6000

tagttaatga tcagcccact gacgcgttgc gcgagaagat tgtgcaccgc cgctttacag   6060

gcttcgacgc cgcttcgttc taccatcgac accaccacgc tggcacccag ttgatcggcg   6120

cgagatttaa tcgccgcgac aatttgcgac ggcgcgtgca gggccagact ggaggtggca   6180

acgccaatca gcaacgactg tttgcccgcc agttgttgtg ccacgcggtt gggaatgtaa   6240

ttcagctccg ccatcgccgc ttccactttt tcccgcgttt tcgcagaaac gtggctggcc   6300

tggttcacca cgcgggaaac ggtctgataa gagacaccgg catactctgc gacatcgtat   6360

aacgttactg gtttcacatt caccaccctg aattgactct cttccgggcg ctatcatgcc   6420

ataccgcgaa aggttttgcg ccattcgatg gtgtccggga tctcgacgct ctcccttatg   6480

cgactcctgc attaggaagc agcccagtag taggttgagg ccgttgagca ccgccgccgc   6540

aaggaatggt gcatgcaagg agatggcgcc caacagtccc ccggccacgg ggcctgccac   6600

catacccacg ccgaaacaag cgctcatgag cccgaagtgg cgagcccgat cttccccatc   6660

ggtgatgtcg gcgatatagg cgccagcaac cgcacctgtg gcgccggtga tgccggccac   6720

gatgcgtccg gcgtagagga tcgagatcga tctcgatccc gcgaaattaa tacgactcac   6780

tata                                                                6784
```

POLYMERASE-IMMOBILIZED ELECTRODE

TECHNICAL FIELD

The present invention relates to a polymerase-immobilized electrode which can be suitably used for obtaining information on a base sequence of a nucleic acid by using an electrochemical reaction.

BACKGROUND ART

Proceedings of National Academy of Sciences, USA, 74: 5,463 to 5,467 (1977) describes a dideoxy method as a method for analyzing a base sequence of a nucleic acid. In addition, Japanese Patent Application Laid-Open No. H05-168500 describes a method of determining a base sequence of a nucleic acid by using the dideoxy method.

However, the above described method of analyzing the base sequence by using the dideoxy method includes a step of separating the extended DNA strands by electrophoresis, and accordingly needs a long period of time for obtaining an analysis result.

In addition, Japanese Published Patent Application No. 2003-189899 describes a method of detecting a base sequence of a nucleic acid, by carrying out a reaction between a target single-standard nucleic acid, a single-stranded nucleic acid probe immobilized on a substrate, DNA polymerase and labeled ddNTP, where the probe is hybridizable with a downstream nucleotide sequence of an SNP site in the single-stranded nucleic acid. However, the above described detecting method has problems that the method needs to wash out the unreacted labeled ddNTP and only one base is identified. Accordingly, the present invention provides a polymerase-immobilized electrode of highly sensitive detection ability, and a method for obtaining the information on a base sequence by using the polymerase-immobilized electrode.

DISCLOSURE OF THE INVENTION

A polymerase-immobilized electrode according to the present invention can be used to obtain the base sequence information of a nucleic acid, by translating the presence or absence of incorporation of a nucleotide derivative into a double stranded part of a nucleic acid into electrical signals. By using a polymerase-immobilized electrode of the present invention, the base sequence information can be taken out as electric signals with high efficiency and sensitivity.

The present invention provides a polymerase-immobilized electrode comprising an electroconductive substrate and a polymerase unit immobilized on the surface of the electroconductive substrate, wherein the polymerase unit comprises a polymerase part, an anchor part and an electroconductive part which are linked in an order of the polymerase part, the anchor part and the electroconductive part, or in an order of the polymerase part, the electroconductive part and the anchor part; and the polymerase unit is immobilized on the electroconductive substrate by the anchor part; and an end of the electroconductive part not immobilized on the electroconductive substrate is located in the vicinity of an active site of the polymerase part.

It is preferable that the polymerase unit comprises the polymerase part, the anchor part and the electroconductive part that are linked in this order, and the length from the free end of the electroconductive part to the end of the anchor part adjacent to the electroconductive part is almost the same as a length from the active site of the polymerase part to an end of the anchor part adjacent to the polymerase part.

It is preferable that a polyhistidine tag and a metal coordinated by the polyhistidine tag are present between the polymerase part and the anchor part, and the polymerase part is linked to the anchor part by coordination bonding between the polyhistidine tag and the metal.

It is also preferable that the polymerase unit comprises the polymerase part, the electroconductive part and the anchor part linked in this order, wherein the electroconductive part is directly bonded to the polymerase part.

It is also preferable that a polyhistidine tag and a metal coordinated by the polyhistidine tag are present between the polymerase part and the electroconductive part, and the polymerase part is linked to the electroconductive part by coordination bonding between the polyhistidine tag and the metal.

Preferably, the electroconductive part is a $\pi$-conjugated metallic complex group.

It is also preferable that the electroconductive part contains a nucleic acid.

Another aspect of the present invention is a method of obtaining base sequence information comprising the steps of:

preparing a sample of a target nucleic acid forming a double stranded portion with a primer, a polymerase-immobilized electrode and a nucleotide derivative having an electrochemically convertible part;

making the sample, the polymerase-immobilized electrode and the nucleotide derivative coexist in a solvent; and detecting whether the nucleotide derivative is introduced in the primer or not, by using an electrochemical reaction; wherein the polymerase-immobilized electrode comprises an electroconductive substrate and a polymerase unit immobilized on the surface of the electroconductive substrate, wherein the polymerase unit comprises a polymerase part, an anchor part and an electroconductive part which are linked in an order of the polymerase part, the anchor part and the electro conductive part, or in an order of the polymerase part, the electroconductive part and the anchor part; and the polymerase unit is immobilized on the electroconductive substrate by the anchor part; and an end of the electroconductive part away from the electroconductive substrate is located in the vicinity of an active site of the polymerase part.

BEST MODES FOR CARRYING OUT THE INVENTION

The present invention provides a polymerase-immobilized electrode comprising an electroconductive substrate and a polymerase unit immobilized on the surface of the electroconductive substrate, wherein the polymerase unit comprises a polymerase part, an anchor part and an electroconductive part; the polymerase part, the anchor part and the electroconductive part are linked in an order of the polymerase part, the anchor part and the electroconductive part, or in an order of the polymerase part, the electroconductive part and the anchor part; and the polymerase unit is immobilized on the electroconductive substrate through the anchor part; and wherein an end of the electroconductive part away from the electroconductive substrate is located in the vicinity of an active site of the polymerase part.

A first embodiment of the polymerase-immobilized electrode of the invention is the above polymerase-immobilized electrode in which the polymerase part, the anchor part and the electroconductive part are linked in this order in the polymerase unit.

A polymerase-immobilized electrode of the first embodiment will be described below.

Figure 1A:
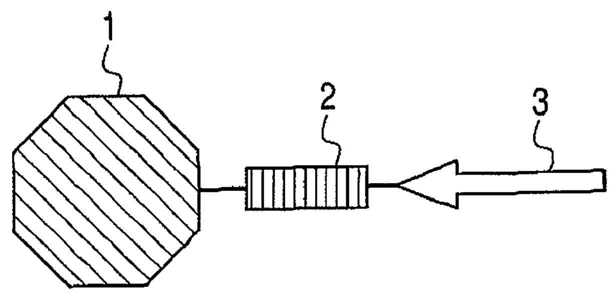
FIGS. 1A, 1B, 1C and 1D are schematic views illustrating configuration examples of a polymerase unit to be used in a polymerase-immobilized electrode of the present invention.

FIG. 1A schematically illustrates an example of a structure of a polymerase unit (a) to be used in a polymerase-immobilized electrode of the first embodiment. In FIG. 1A, a polymerase unit (a) comprises a polymerase part 1, an anchor part 2 and an electroconductive part 3 which are linked in this order in series.

Figure 2A:
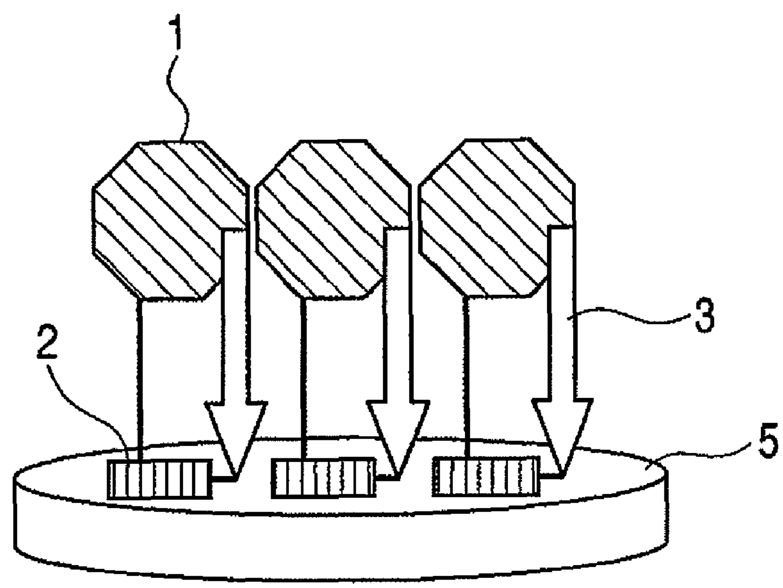
FIGS. 2A, 2B, 2C and 2D are schematic views illustrating configuration examples of a polymerase-immobilized electrode of the present invention.

FIG. 2A schematically illustrates an example of a polymerase-immobilized electrode which uses a polymerase unit (a). The polymerase-immobilized electrode comprises a polymerase unit (a) having polymerase 1, an anchor part 2 and an electroconductive part 3 linked in this order; and an electroconductive substrate 5. The polymerase unit (a) is immobilized on the electroconductive substrate 5 through the anchor part 2 of the polymerase unit (a). The polymerase-immobilized electrode can electrochemically discriminate the base type of the extended nucleotide at the end, when a nucleic acid complementary to the target nucleic acid contained in the polymerase-immobilized electrode is synthesized.

As shown in FIG. 2A, a polymerase-immobilized electrode of the first embodiment has a polymerase unit (a) immobilized by an anchor part 2 existing between a polymerase part 1 and an electroconductive part 3. By forming such a structure, the electroconductive part 3 of the polymerase unit (a) can be arranged in the vicinity of the polymerase part 1.

Specifically, by designing the following lengths A and B to be approximately equal, the end of the electroconductive part 3 away from the above described electroconductive substrate 5 tends to locate in the vicinity of an active site of the above described polymerase part (1);

(A): the length between a free end of the electroconductive part 3 (an end away from the electroconductive substrate) and the end of the anchor part 2 proximal to the part 3 and (B): the length between an active site of the polymerase part 1 and the end of the anchor part 2 proximal to the polymerase part (between the nucleotide derivative attached to the 3'-terminus of the extended chain in the part 1 and the end of the anchor part 2 proximal to the polymerase part 1).

Preferably, the above polymerase part (1) is designed such that the length (A) is shorter than the length (B) by 5 nm or less. This is because, if the length (B) is longer than the length (A), nucleotide may hardly be captured by a polymerase part due to the steric hindrance of the electroconductive part.

Here, in the present invention, "in the vicinity" means being within 5 nm or less. In addition, an expression that lengths (A) and (B) are approximately equal means that a difference between the length of (A) and the length of (B) is 5 nm or less.

The length between the free end of the electroconductive part 3 and the end of the anchor part 2 proximal thereto is a length between the free end of the electroconductive part 3 and the bonding site of the anchor part 2 and the electroconductive part 3, when the anchor part 2 and the electroconductive part 3 are directly bonded. When a first linker is present between the anchor part 2 and the electroconductive part 3, the above described length means a length between the free end of the part 3 and the coupling site of the anchor part 2 and the first linker.

Thereby, electrochemical conversion of a nucleotide derivative attached to the 3'-terminus of an extended chain becomes possible at a lower overvoltage than before. As a result, false signals can be reduced which are caused by electrochemical conversion of the unreacted nucleotide 5'-triphosphate derivative remaining in the solution on the electrode. In order to further reduce the contribution of the false signals, the electroconductive substrate may be subjected to blocking treatment after immobilization of the polymerase unit on the substrate. Usable blocking treatment includes, for instance, immersion of the electroconductive substrate having a polymerase unit immobilized thereon into an aqueous solution of protein such as bovine serum albumin and casein. Alternatively, the electroconductive substrate having a polymerase unit immobilized thereon may be immersed in an aqueous solution containing a similar compound having the same coupling type as the anchor part, for instance, when the anchor part is disulfide, a compound having disulfide or thiol as a functional group.

Next, each part composing the polymerase-immobilized electrode will be described with reference to FIG. 2A. As described above, a polymerase unit has a polymerase part 1, an anchor part 2 and an electroconductive part 3 as basic elements. The polymerase part 1 is a part for synthesizing a complementary nucleic acid using a target nucleic acid as a template, i.e., a polymerase. Such a polymerase is selected in accordance with a type of the nucleic acid from which information is obtained. For instance, when the nucleic acid is DNA, the polymerase to be selected is DNA-dependent DNA polymerase (EC 2.7.7.7) or DNA-dependent RNA polymerase (EC 2.7.7.6). When the polymerase is a DNA dependent DNA polymerase, it catalyzes a reaction shown in the following expression (1), and when the polymerase is a DNA dependent RNA polymerase, it catalyzes a reaction shown in the following expression (2):

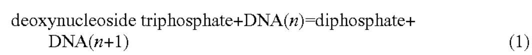

deoxynucleoside triphosphate+DNA($n$)=diphosphate+DNA($n$+1) (1)

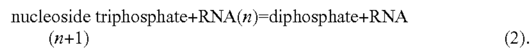

nucleoside triphosphate+RNA($n$)=diphosphate+RNA($n$+1) (2).

On the other hand, when the type of the nucleic acid on which information acquisition is intended is RNA, the selected polymerase is RNA-dependent DNA polymerase (EC 2.7.7.49) or RNA-dependent RNA polymerase (EC 2.7.7.48). When the polymerase is an RNA-dependent DNA polymerase, it catalyzes a reaction shown in the following expression (3), and when the polymerase is an RNA-dependent DNA polymerase, it catalyzes a reaction shown in the following expression (4):

nucleoside triphosphate+RNA($n$)=diphosphate+RNA($n$+1) (3)

deoxynucleoside triphosphate+DNA($n$) diphosphate+DNA($n$+1) (4).

The source of the polymerase is not limited. In addition, it is preferable that the polymerase lacks 3'→5' exonuclease activity. This is because the extended nucleic acid chain is not decomposed even when nucleoside 5'-triphosphate is depleted.

An active site of a polymerase in the polymerase part 1 is an amino acid sequence having homology to a motif sequence: Asp Tyr Ser Gln Ile Glu Leu Arg Val Leu Ala His Leu [SEQ ID NO: 11], and a motif sequence: Arg Met Leu Leu Gln Val His Asp Glu Leu [SEQ ID NO: 12], when the amino acid sequence of the polymerase to be used and that of DNA polymerase family A: pfam00476 are aligned with two aspartic acid residues existing in the palm domain of the polymerase or homologous amino acids, where pfam00476 is in a sequence homology database about a protein family and domains (Pfam) (Nucleic Acids Research, 2006, Vol. 34, Database issue D247-D251).

The anchor part 2 has a function of immobilizing the polymerase unit (a) on the surface of the electroconductive substrate 5. In other words, the polymerase unit (a) is immobilized on the surface of the electroconductive substrate 5 by the anchor part 2.

The anchor part 2 is defined as a portion immobilized on the electroconductive substrate. Such an anchor part 2 may be an atom, an atomic group or a functional group, which can form a covalent bond with the electroconductive substrate or may be a biological molecule having affinity for the electroconductive substrate.

More specifically, disulfide group is a representative of such an atom, atomic group or functional group that can form a covalent bond with the electroconductive substrate. When the functional group is a disulphide group, the electroconductive substrate is preferably made of a gold-containing material. The biological molecule having an affinity to the electroconductive substrate may be a peptide, an antibody fragment, nucleic acid, an aptamer or a sugar chain. When a portion of the peptide or the like is immobilized on the electroconductive substrate, the immobilized part is defined as an anchor part, and the remaining portion not immobilized is defined as a linker portion.

The length of the anchor part 2 can be varied according to the type of the polymerase part used, but it is preferable that it is smaller than the polymerase part 1. This means that the longest segment of the anchor part 2 is smaller than the diameter of the polymerase part 1. Here the diameter (Φ) of the polymerase part 1 is defined as the diameter of a sphere circumscribed on the polymerase part or the diameter of a sphere having a surface area that is equal to the exposed surface area of the polymerase part, whichever is greater; or when the crystal structure of the polymerase part is not known, it is defined by the following expression:

$$\phi = 0.1\sqrt{\frac{6.3M^{0.73}}{\pi}}$$

wherein the unit is nm, and M represents the molecular weight of the polymerase part.

When the anchor part 2 is larger than the polymerase part 1, the density of the polymerase part 1 becomes low with respect to the surface of an electroconductive substrate 5 (hereafter may be referred to as an electrode surface), which may result in weak signal intensity. In such a case, the exposed area (not covered with the polymerase part 1) increases in the electrode surface, and consequently, unreacted nucleotide derivatives can easily access to the electrode, which may increase noise.

For instance, when using a Klenow fragment of *E. coli* DNA polymerase I as a polymerase part 1, the size of the anchor part 2 is preferably 8.2 nm or less.

In view of facilitation of immobilization of the anchor part 2 onto the substrate 5, the anchor part 2 preferably has a higher binding ability to the substrate 5 than to the remaining portion of the polymerase unit (a) (the polymerase part (1) and the electroconductive part (3)). Having such a structure, the polymerase unit (a) can be easily immobilized onto the electroconductive substrate 5 by the anchor part 2. It is preferable to adjust the structures of these parts so that the polymerase part 1 and the electroconductive part 3 have difficulty in binding to the substrate 5 and the anchor part 2 readily binds to the substrate 5. Even if such adjustment is difficult, the constitution of the present invention is effective. For example, the polymerase unit can be immobilized on the electroconductive substrate through the anchor part as follows: a portion of the polymerase unit including the anchor part but not a portion having a substrate 5-binding ability higher than the anchor part is immobilized to the electrode surface, and then the remaining portion having a higher binding ability to the substrate 5 than the anchor part is coupled to the previously immobilized portion.

Next, the electroconductive part 3 will be described.

The electroconductive part 3 transfers electrons between the polymerase part 1 and the electroconductive substrate 5, and is linked to the anchor part 2 which is also bonded to the electroconductive substrate 5, thus electrically conductive with the electroconductive substrate 5. As the polymerase unit (a) has the electroconductive part 3, electrochemical conversion of the nucleotide derivative attached to the 3' end of the extended strand can be carried out at a low overvoltage, when information acquisition using a nucleotide derivative having an electrochemically convertible portion described later. The above description that "(A) is electrically conductive with B" means that an electric resistance value between A and B is $1.0\times10^{20}\Omega$ or less.

The electroconductive part 3 may be directly coupled with the anchor part 2, or indirectly coupled with it through a linker. Such an electroconductive part 3 may have one of the following structures:

<1> A construct composed of an electroconductive substance and a bar-shaped organic molecule having electroconductivity, where "bar-shaped" means a shape similar to a cylinder or a prism, in which the part corresponding to the height of the cylinder at the prism is twice or more as long as the other sides or the diameter; and the above description "having electroconductivity" means electroconductivity is $10^{-6}$ S/cm or higher;

<2> A construct of the above <1>, in which the electroconductive substance is held, at least, in an inner part, at an end or on a peripheral surface of the above described bar-shaped organic molecule;

<3> A construct of <1> or <2>, in which the bar-shaped organic molecule is selected from α-helixed protein, DNA and amylase;

<4> A construct of any one of <1>-<3>, in which the electroconductive substance contains at least one substance selected from a metal atom, a metallic oxide, a metal sulfide and a carbon compound;

<5> A construct of any one of <1>-<4>, in which the electroconductive substance is a dopant used for doping of a π-conjugated aromatic polymer;

<6> A construct of <5>, in which the dopant is at least one compound selected from an electroconductive polymer such as polyaniline, polythiophene, polypyrrole, polyphenylenevinylene and polyacene; a Lewis acid; a protonic acid; a halide of a transition metal; an alkali metal; an alkylammonium ion; a surface active agent; and an amino acid; and <7> A construct of any one of <1> to <6>, in which the electroconductive substance is a π-conjugated metallic complex molecule, a molecule having a complex skeleton made of a central metal and π-conjugated ligands. A transition metal element can be used for the central metal of the complex. The transition metal element includes, for instance, Cs, Fe, Ru, Co, Cu, Ni, V, Mo, Cr, Mn, Pt, Rh, Pd and Ir. Any compound can be used as a π-conjugated ligand as long as it has a π-conjugated electrons spreading over the molecule skeleton, sufficient chemical stability and coordinating capability under conditions in which the electrode is used in an aqueous solution. For instance, the ligand may be bipyridine, terpyridine, phenanthroline, porphyrin, phthalocyanine or a derivative thereof.

The electroconductive part 3 may be composed of plural regions of different properties. Here, "region" means a particular range which can be mutually discriminated according to a property such as electroconductivity.

Figure 1B:
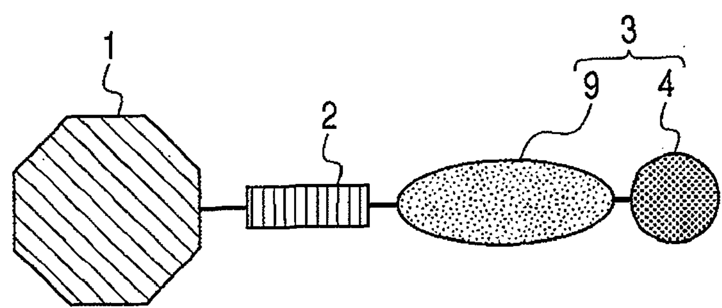

Such a structure of the polymerase unit (a) is schematically illustrated in FIG. 1B, where the electroconductive part 3 has a first electroconductive region 9 near the electroconductive substrate, and a second electroconductive region (hereafter, may be referred to as a probe region) 4 near the free end.

Figure 2B:
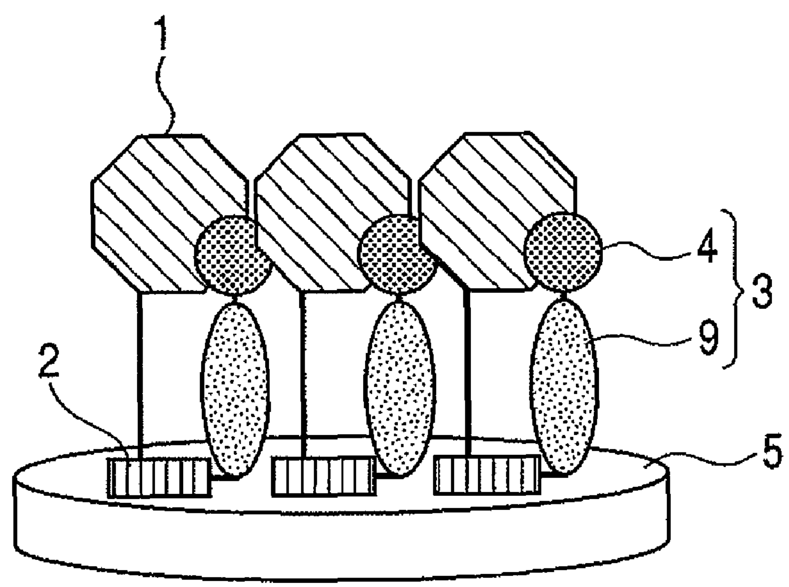

Another structural example of a polymerase-immobilized electrode of the first embodiment is illustrated in FIG. 2B, in which the electroconductive part 3 has a probe region 4. When the polymerase-immobilized electrode has a small second electroconductive region 4 in addition to the first electroconductive region 9, the polymerase-immobilized electrode can transfer electrons even when the first electroconductive region 9 is so large that when the electroconductive part comprises only the large first electroconductive region 9 it is difficult for the free end of the first region 9 to access a nucleotide derivative added to the extended chain end in the polymerase. However, in the above case, it is preferable to adjust the length of the first electroconductive region 9 so that the free end of the above described probe region 4 comes in the vicinity of a nucleic acid extension reaction site in the polymerase part 1. When the above polymerase unit has such a structure, the free end of the electroconductive part (free end of the second electroconductive region) is arranged in the physical vicinity of the 3'-end of the extended chain in the polymerase molecule, as with the case where the electroconductive part is formed of one region. Thus electrochemical conversion of the nucleotide derivative added to the 3' end of the extended chain at a low overvoltage becomes easier.

In other words, such a structure can further reduce the overvoltage required for electrochemical conversion of a nucleotide derivative having an electrochemically convertible capping structure at the extension end.

The probe region 4 can be constituted of: microparticles of Au, Pt, Ag, Co, Pd, Rh, Ni, Cr, Fe, Mo, Ti, Cu, W and an alloy thereof; a compound having a quinone skeleton, such as ACNQ (2-amino-3-carboxy-1,4-naphthoquinone), phylloquinone, menaquinone and menadione; a metallic complex of Os, Ru, Fe and Co; a viologen compound such as benzil viologen; a compound having a nicotinamide structure; a compound having a riboflavin structure; and a compound having a nucleotide-phosphate structure. The probe region 4 can also include two or more types of these materials in combination, as needed. Preferably, the probe region 4 is as small as to be able to access to the nucleotide derivative added to the end of the extended strand in the polymerase part 1. Its size is preferably about 0.5 nm to 2 nm.

The electroconductive substrate 5 can be made of a material which has electroconductivity and sufficient electrochemical stability under the use conditions of the electrode, specifically, on the condition in which a polymerase part 1 has enzyme activity. Examples of such a material for the electroconductive substrate 5 are a metal, an electroconductive macromolecule, a metallic oxide or a carbon material. An example of the metal is one containing at least one element of Au, Pt, Ag, Ni, Cr, Fe, Mo, Ti, Al, Cu, V, In, Ga and W, which may be an alloy or plate. An example of the electroconductive polymer is one containing at least one compound selected from a polyacetylene, a polyarylene, a polyarylenevinylene, a polyacene, a polyarylacetylene, a polydiacetylene, a polynaphthalene, a polypyrrole, a polyaniline, a polythiophene, a polythienylenevinylene, a polyazulene and a polyisothianaphthene. An example of the metallic oxide is one containing at least one metallic element selected from In, Sn, Zn, Ti, Al, Si, Zr, Nb, Mg, Ba, Mo, W, V and Sr. An example of the carbon material is graphite, carbon black, a carbon nanotube, a carbon nanohorn, a fullerene compound, or a derivative thereof.

A linker may exist in the connecting site between the above described respective parts (between the polymerase part 1, anchor part 2 and electroconductive part 3, and between the first electroconductive region and the second electroconductive region in the electroconductive part 3), as long as the desired function is not damaged. A connection method between the respective parts adjacent to each other can be selected according to the type of the molecules composing the respective parts and the use of the polymerase-immobilized electrode. The connection method is not limited in particular as long as the connection has sufficient chemical and electrochemical stability under the conditions of polymerase unit preparation, immobilization of the polymerase unit on the electrode and the use of the electrode in an aqueous solution, for instance. The method for connecting the respective parts may utilize covalent bonding, coordinate bonding, hydrogen bond, electrostatic interaction, hydrophobic interaction, or physical adsorption.

Figure 3A:
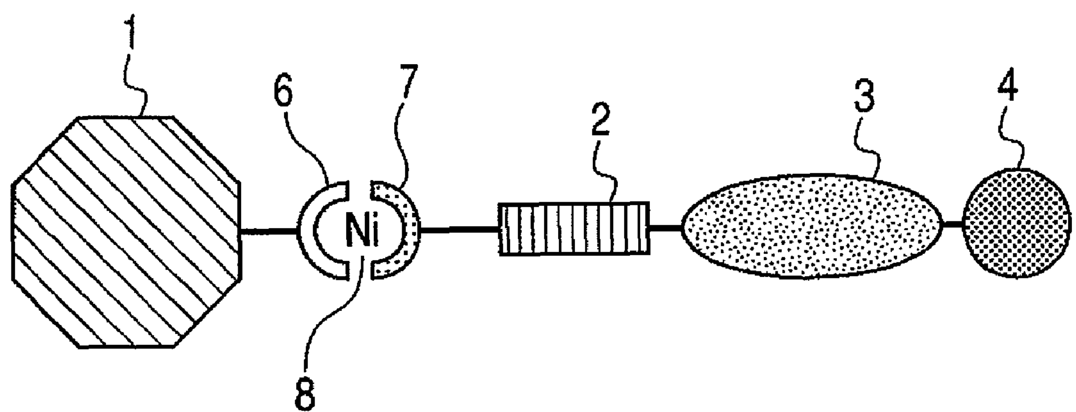
FIGS. 3A and 3B are schematic views illustrating other configuration examples of a polymerase unit to be used in a polymerase-immobilized electrode of the present invention.

Alternatively, the polymerase part 1 can be linked to the anchor part 2 by using a polyhistidine tag. FIG. 3A schematically illustrates such an example. In this case, a linker between the polymerase part 1 and the anchor part 2 is composed of a polyhistidine tag 6, a central metal part 8 to which the polyhistidine tag 6 coordinates (in FIG. 3A, nickel ion) and an NTA (nitrilotriacetic acid) 7.

Figure 4A:
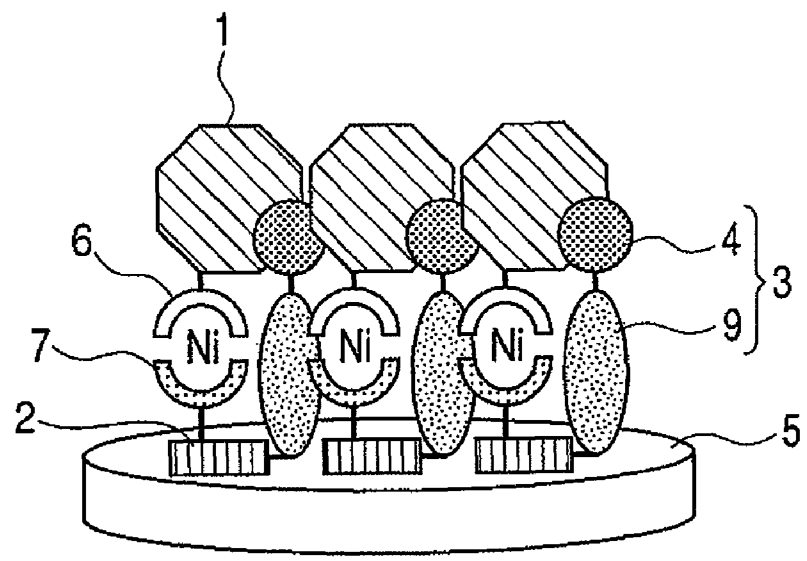
FIGS. 4A and 4B are schematic views illustrating other configuration examples of a polymerase-immobilized electrode of the present invention.

Conveniently, it allows separate preparation of a fused polymerase-histidine tag portion (in this case, the polymerase part 1 and the polyhistidine tag 6), and a portion for making up the probe-modified polymerase (a portion consisting of a probe part 4, an electroconductive part 3, the anchor part 2 and the NTA7). FIG. 4A schematically illustrates a state where the polymerase unit is bound to the electroconductive substrate using a polyhistidine tag. Even when the polyhistidine tag is used, the free end of the probe region 4 should come near to the active site of the polymerase part 1 as described above. Accordingly, it is preferable that the length between the free end of the probe region 4 and the end of the anchor part 1 proximal thereto is approximately equal to the length between the nucleotide derivative attached to the 3'-extending end of the polymerase part 1 and the end of the anchor part 2 proximal to the polymerase part 1. The term "approximately equal" is as defined above.

Next, a second embodiment of the polymerase-immobilized electrode will be described.

In the second embodiment, the polymerase unit (b) in the polymerase-immobilized electrode is composed of a polymerase part, an anchor part and an electroconductive part that are linked in this order. The polymerase unit (b) has the same structure as in a first embodiment except that the connection order of the polymerase part, the electroconductive part, and the anchor part.

Figure 1C:
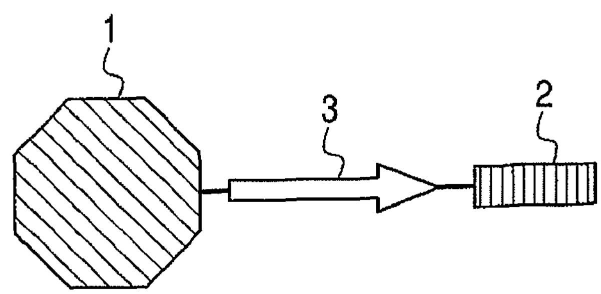
Figure 2C:
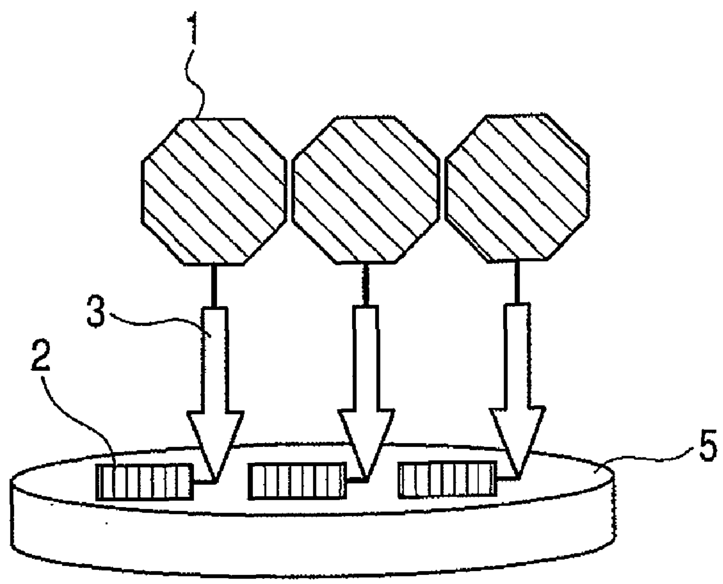

FIG. 2C illustrates an example of a polymerase-immobilized electrode of the second embodiment. In addition, FIG. 1C illustrates an example of a polymerase unit (b) to be used in the polymerase-immobilized electrode of the second embodiment.

The polymerase unit (b) includes a polymerase part 1, an electroconductive portion 3 and an anchor part 2, which are linked in this order, and is immobilized on an electroconductive substrate 5 by the anchor part 2.

A polymerase-immobilized electrode of the second embodiment also provides the same effect as the first polymerase-immobilized electrode, by positioning the electroconductive part 3 physically in the vicinity of the polymerase part 1. In order to make such a structure, a coupling site between the electroconductive part 3 and the polymerase part 1 is preferably in the vicinity of the active site of the polymerase part 1. As a result, the electroconductive part 3 can locate physically in the vicinity of the 3'-end of an extended chain inside the polymerase molecule, which enables electrochemical conversion of a nucleotide derivative added to the 3'-end of the extended chain at a low overvoltage, as with the polymerase-immobilized electrode of the first embodiment. In other words, the electrode can electrochemically convert the nucleotide derivative added to the 3'-end of an extended chain at an overvoltage lower than before, which reduces false signals due to the electrochemical conversion of unreacted nucleotide 5'-triphosphate derivatives remaining in the solution.

Figure 1D:
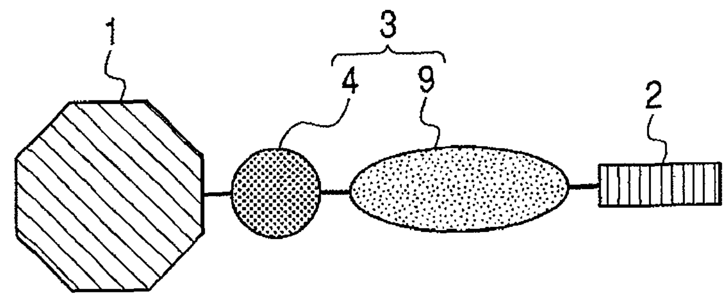
Figure 2D:
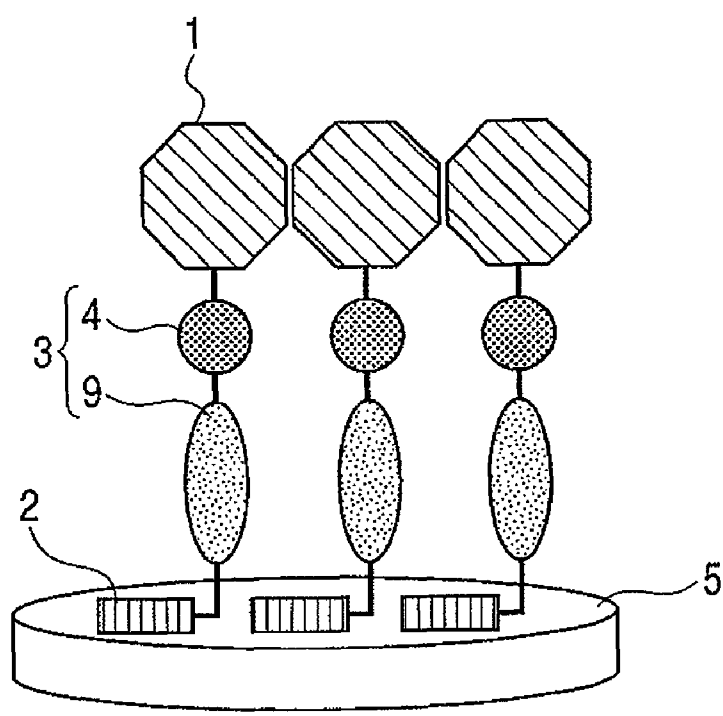

In addition, the electroconductive part of the polymerase unit (b) may be composed of a plurality of regions, as with the polymerase-immobilized electrode of the first embodiment. FIG. 1D illustrates a polymerase unit (b) which has an electroconductive part 3 between a polymerase part 1 and an anchor part 2 where the electroconductive part 3 is composed of a first electroconductive region 9 adjoining the anchor part and a second electroconductive region (probe region) 4 adjoining the polymerase part. A polymerase-immobilized electrode using such a polymerase unit is illustrated in FIG. 2D. When having such a structure, the polymerase-immobilized electrode enables easier electrochemical conversion of a nucleotide derivative added to the 3'-end of an extended chain, at a low overvoltage.

Figure 3B:
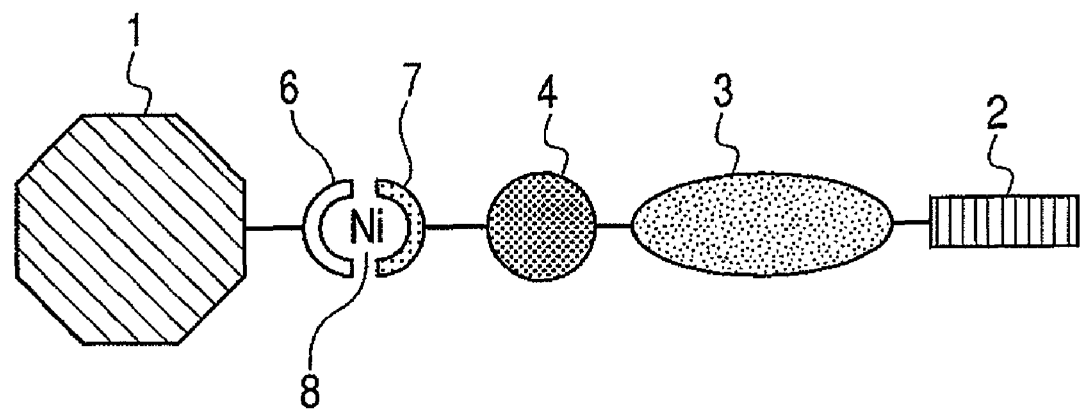
Figure 4B:
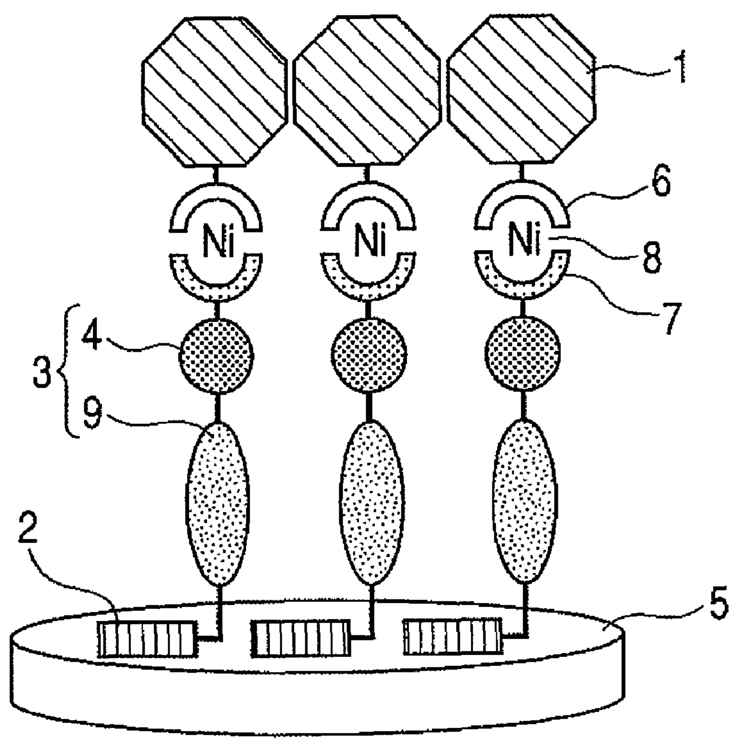

Preferably, an electroconductive part 3 is directly linked to a polymerase part 1, but it may be linked through a linker. When a linker exists, the length of the linker may be preferably 2 nm or shorter. Also, as with the polymerase unit (a), it is possible to link the polymerase part 1 and the probe part 4 of the polymerase unit (b) using the coordination bond between the polyhistidine tag and a metal as shown in FIG. 3B. A polymerase-immobilized electrode formed using the polymerase part (b) shown in FIG. 3B has a constitution as shown in FIG. 4B.

Next described is a method for obtaining a base sequence by using a polymerase-immobilized electrode (a) or (b). The method for obtaining the base sequence using the polymerase-immobilized electrode can be applied, for instance, to confirmation diagnosis of the base sequence of a predetermined part.

The polymerase-immobilized electrode according to the present invention can be suitably used to obtain information on a base sequence by using incorporation of nucleotides into a double-stranded nucleic acid (incorporation of nucleotides to the 3'-end of a complementary strand when one strand is used as a template) by polymerase. Such an information acquisition method includes the following embodiments. In the following, exemplified steps in the base sequence analysis method according to the present invention are described referring to FIGS. 5(1)-5(4).

A) First Embodiment

Figure 5:
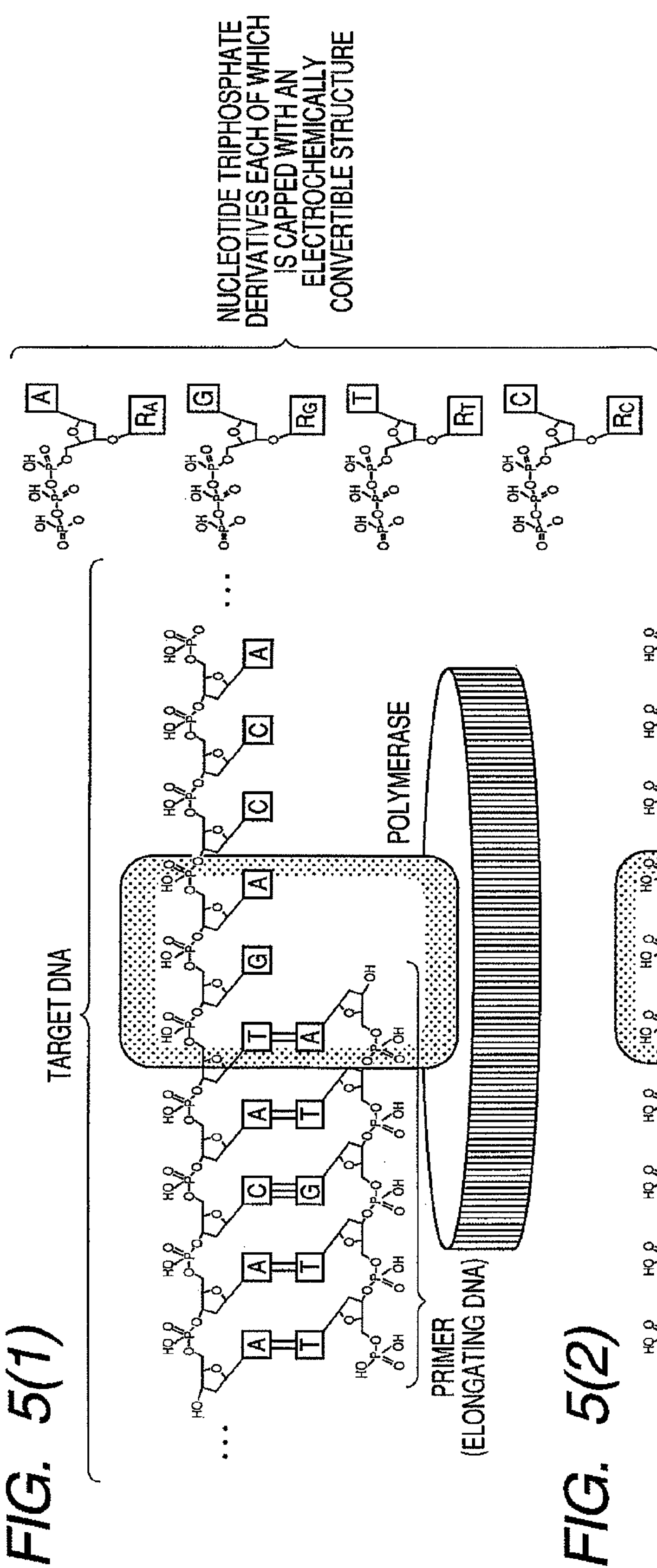
FIGS. 5(1), 5(2), 5(3) and 5(4) are schematic views for describing each step in a method for analyzing a base sequence of a nucleic acid using a polymerase-immobilized electrode of the present invention.
Figure 5:
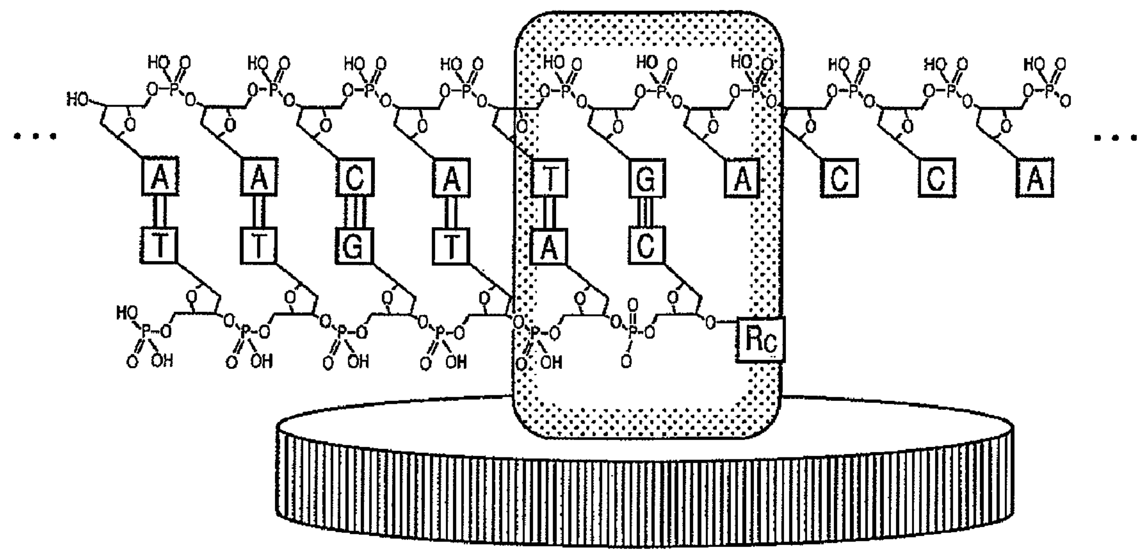
Figure 5:
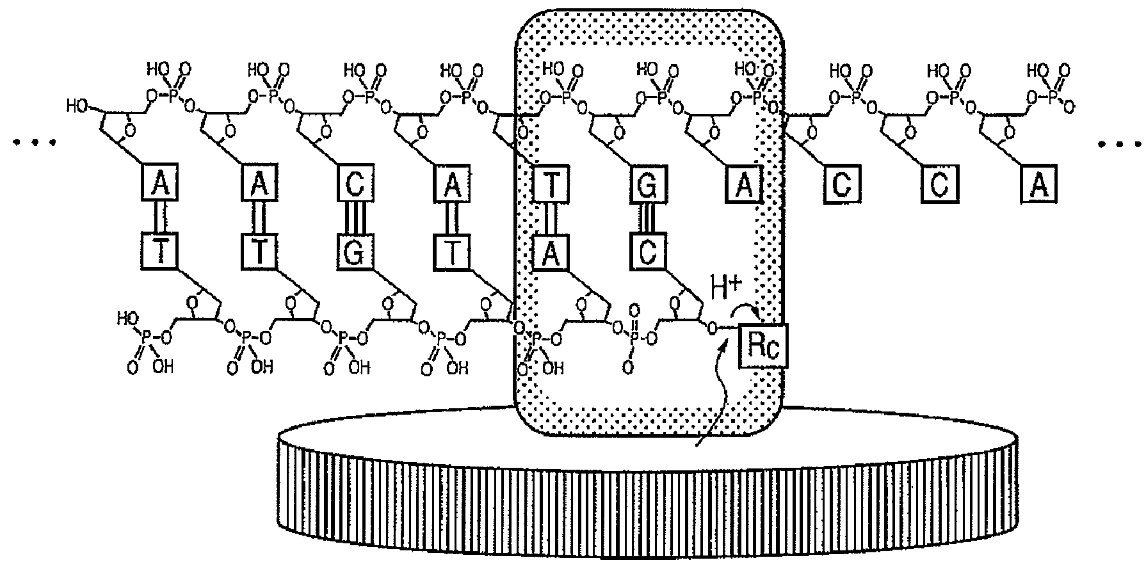

First, the followings are provided: a double-stranded sample being a target nucleic acid strand and a primer hybridized thereto, a polymerase-immobilized electrode and a nucleotide derivative having an electrochemically convertible portion (FIG. 5(1)). Here, "electrochemical conversion" means removal of a portion, chemical bond cleavage or reconstruction of the above-described derivative caused by the electron transfer through the electroconductive substrate.

The nucleotide derivative is, for example, a nucleoside 5'-triphosphate derivative, including at least the following substances:

adenosine 5'-triphosphate derivatives,
cytidine 5'-triphosphate derivatives,
guanosine 5'-triphosphate derivatives,
uridine 5'-triphosphate derivatives,
2'-deoxyadenosine 5'-triphosphate derivatives,
2'-deoxycytidine 5'-triphosphate derivatives,
2'-deoxyguanosine 5'-triphosphate derivatives, and
2'-deoxythymidine 5'-triphosphate derivatives.

The nucleotide derivatives described above as examples can be used also in the embodiment (B) and later embodiments. In the FIG. 5, plurality types of the nucleotide derivatives are illustrated, but single or plural types of derivatives may be used, as needed.

Then, the double-stranded sample, the polymerase-immobilized electrode and the nucleotide derivative are put in a solvent (FIG. 5(1)). Here, the solvent is a water-soluble liquid or a gelatinous substance to hold the sample, the polymerase-immobilized electrode and the nucleotide derivative. When the base of the nucleotide derivative is complementary to the base of the target nucleic acid strand next to the 3'-end of the primer in the sample, the nucleotide derivative is introduced into the 3'-end of the primer (FIGS. 5(2) and 5(3)); if not complementary, the derivative is not introduced into the 3'-end of the primer. Subsequently, whether the nucleotide derivative is introduced into the primer or not is detected by using an electrochemical reaction.

For instance, when only one type of the nucleotide derivative is present with the sample, and the nucleotide derivative is introduced into the sample, it is assumed that a base corresponding to the nucleotide derivative exists in the predetermined part. On the other hand, when it is not introduced, it is assumed that a base corresponding to the nucleotide derivative does not exist at least in the predetermined part. By such, the information on the base sequence of the target nucleic acid can be obtained.

This method can provide information on the type of the base existing at a predetermined position (adenine (A), cytosine (C), guanine (G) or thymine (T)). It can also provide such information that what base is not present at a predetermined position (for instance, not (A)). The above description is similarly applied to the following embodiments as well.

As described above, "conversion" in an electrochemically convertible portion of the nucleotide derivative means cleavage or reconstruction of a chemical bond caused by electron transfer through the electroconductive substrate. The above described "conversion" also includes elimination or substitution of, or addition to the portion or a higher group including the portion of the nucleotide derivative. In the nucleotide derivative, "the electrochemically convertible portion" means a portion that can be subjected to elimination, substitution, or addition by the electrochemical reaction. As an electrochemically active functional group (which gives or receives electrons to or from an electroconductive substrate), there is a group formed of a metallic complex, for instance. However, in the metallic complex, only the oxidation number of a central metal changes according to oxidation or reduction, and cleavage or restructure of a chemical bond does not occur. Such a group is not referred to as the electrochemically convertible portion in the present invention. The above description is similarly applied to the following embodiments as well.

B) Second Embodiment

A method for reading a base sequence of a target nucleic acid is described.

First, the followings are provided: a double-stranded sample being a target nucleic acid strand hybridized with a primer, a polymerase-immobilized electrode; and a plural types of nucleotide derivatives each having an electrochemically convertible portion having different electrical characteristics from each other. The term "having different electrical characteristics" means that each nucleotide derivative has a different number of electrons and applied voltage necessary for electrochemical conversion from each other, so that they can be distinguished from each other by ordinary electrochemical measurement means.

Then, the sample, the polymerase-immobilized electrode and the nucleotide derivatives are put in a solvent. Thereby, the nucleotide derivative having a base complementary to the given base of the target nucleic acid is polymerized in a 3'-end of a primer. In the above step, the electrochemically convertible portion in the nucleotide derivative is designed to prevent further extension reaction of the primer by the polymerase part constituting the electrode. As a result, even when a plurality of molecules of the target nucleic acid exist in the solvent, the total synthesis reaction is synchronized, because the polymerization reaction stops every time one base is extended.

Then, the nucleotide derivative introduced into the 3'-end of the primer is identified by electrochemical conversion of the electrochemically convertible portion. Here, the electrochemically convertible portion is designed such that as a result of electrochemical conversion (elimination, substitution or addition reaction), the extension reaction by the polymerase part of the polymerase-immobilized electrode starts again.

After the identification step, the polymerase part resumes the extension reaction spontaneously. Accordingly, the base sequence of the target nucleic acid can be determined by repeating the above described identification step after waiting for a period necessary for the polymerase part to extend another base. The extension reaction by polymerase is generally finished in one five-hundredth of a second per single base, so that the process can decode the base sequence at a high speed.

C) Third Embodiment

First, the followings are provided to put them in a solvent: a double-stranded sample being a target nucleic acid and a primer hybridized thereto, a polymerase-immobilized electrode and a nucleotide derivative having an electrochemically convertible portion. Then, an electric signal is detected from an electroconductive member which is electrically in contact with the solvent. The above electric signal is generated from the conversion of the above described part of the nucleotide derivative introduced into the primer by an electrochemical reaction.

Next, a specific example of a method for obtaining information on a base sequence according to the above described first to third embodiments is further described.

A target nucleic acid to be used in the present invention may be DNA, RNA, deoxyribooligonucleotides or ribooligonucleotides. The target nucleic acid may be single stranded or double stranded. In addition, purification of the target nucleic acid is not always necessary. In other words, a sample may be a biological sample containing the target nucleic acid.

A primer to be used in the present invention is an oligonucleotide hybridizable with the target nucleic acid, when the target nucleic acid is DNA or RNA. Its length is not particularly limited, but the oligonucleotide has a length of about 15-mer to 60-mer. The primer is used to make double stranded the 3' region downstream the aimed position of the target strand, of which position information is desired to acquire (target base). The base sequence of the primer recognizes the whole region or part of the 3'region downstream the target base. When using a primer that recognizes part of the 3' region, the extension reaction is carried out in advance to the position corresponding to one base downstream the target base, before used in the incorporation reaction of a nucleotide derivative by the polymerase part in the polymerase-immobilized electrode described later.

Figures 6A, 6B, 7:
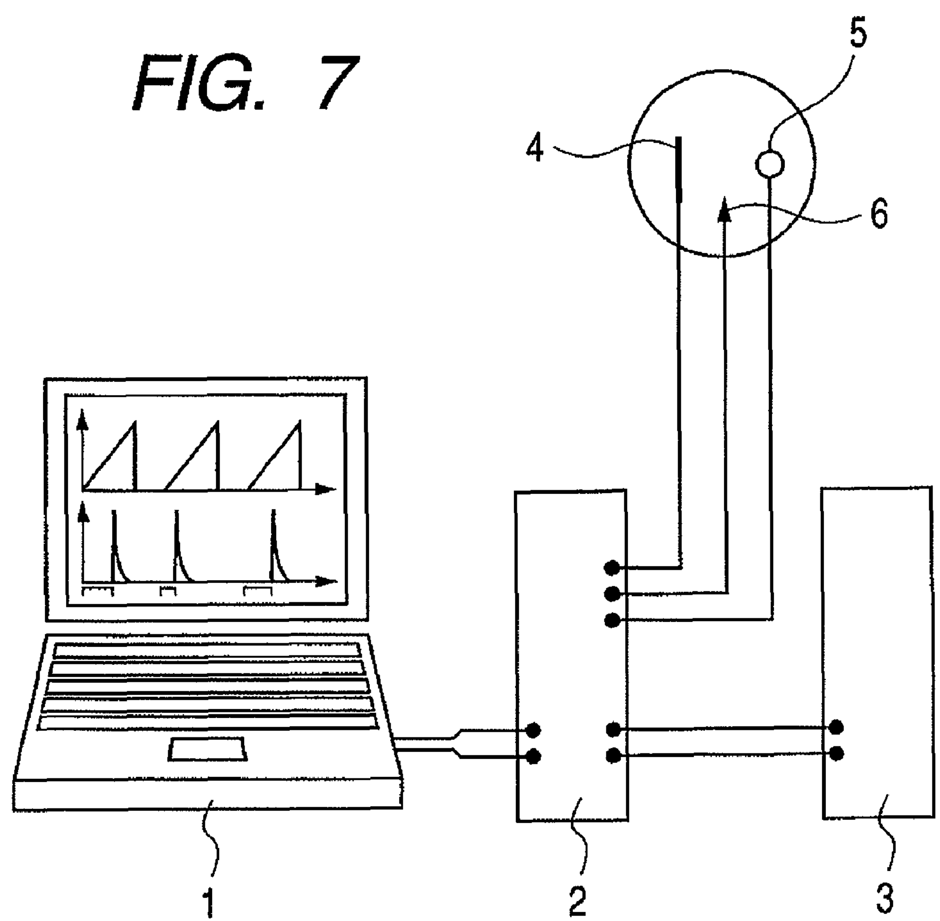
FIGS. 6A and 6B are illustrating a recognition site of a primer on a target nucleic acid.
FIG. 7 is a schematic view illustrating a configuration example of a DNA base sequence analyzer for carrying out analysis of a base sequence in a nucleic acid according to the present invention. Numeral 1 denotes a data processing apparatus, numeral 2 a potentiostat, numeral 3 a function generator, numeral 4 a counter electrode, numeral 5 a polymerase-immobilized electrode, and numeral 6 a reference electrode.

For instance, when the base sequence of which information to be acquired is 3'-$X_1X_2X_3X_4X_5X_6$-5' and the sequence of its 3' region is 3'-G . . . AACAT-5', as illustrated in FIG. 6A, a primer having a base sequence of 5'-C . . . TTGTA-3' which is complementary to the 3'-G . . . AACAT-5' is hybridized to the 3'-region flanking the base $X_1$. Thereby, the 3'-region flanking the target region is made double-stranded. On the other hand, as shown in FIG. 6B, when the 3'-region of the target region is 3'-G . . . AACAT-5' and a primer is C . . . TTGT which recognizes 3'-region two base downstream the target base sequence $X_1X_2X_3X_4X_5X_6$, "A" is added to the primer by an extension reaction. Thereby, the 3'-region downstream the base $X_1$ can be made double-stranded. In the case of FIG. 6B, when the primer recognizes 3'-region three bases downstream $X_1$, the primer is sequentially extended at the 3'-end up to one base downstream $X_1$.

A method for obtaining information by using a primer having a base sequence which recognizes the whole area of a 3'-region includes the method comprising the following steps of:

(1) providing a target nucleic acid, a primer that recognizes the entire 3'-region downstream the target sequence and forms a double-stranded part with the 3'-region, a polymerase-immobilized electrode and a nucleotide derivative having a substituent for measurement;

(2) forming a double-stranded part by hybridizing the above described primer to the 3'-region including one base downstream the target position;
(3) reacting the double-stranded target nucleic acid with the above described nucleotide derivative in the presence of the above described polymerase-immobilized electrode; and
(4) acquiring information on the base at the target position by utilizing the substituent of the nucleotide derivative for measurement, specifically, by detecting whether or not the above described nucleotide derivative has been incorporated at the 3' end of the primer at a position corresponding to the base at the target position.

A method for obtaining information by using a primer having a base sequence which recognizes part of a 3'-region includes the method comprising the following steps of:
(1) providing a target nucleic acid, a primer that recognizes the 3'-region downstream the target sequence by two bases and forms a double-stranded part with the 3'-region, a polymerase-immobilized electrode and a nucleotide derivative having a substituent for measurement;
(2) hybridizing the primer with the target nucleic acid;
(3) extending the 3'-end of the primer hybridized to the target nucleic acid to make the 3'-region downstream the target position of the target strand double-stranded;
(4) reacting the double-stranded target nucleic acid with the nucleotide derivative in the presence of the polymerase-immobilized electrode; and
(5) acquiring information on the base at the target position by utilizing the substituent of the nucleotide derivative for measurement, specifically, by detecting whether or not the above-described nucleotide derivative has been incorporated at the 3' end of the primer at a position corresponding to the base at the target position.

In the present invention, the type of the polymerase part constituting the polymerase-immobilized electrode is selected according to the types of the target nucleic acid and the nucleic acid to be extended. As described above, when a nucleic acid to be extended is DNA, DNA polymerase (nucleic-acid-dependent DNA polymerase) is selected; and when a nucleic acid to be extended is RNA, RNA polymerase (nucleic-acid-dependent RNA polymerase) is selected. When the target nucleic acid is DNA or deoxyribooligonucleotide, the polymerase to be selected and used is DNA-dependent DNA polymerase or DNA-dependent RNA polymerase. When the target nucleic acid is RNA or ribooligonucleotide, the polymerase to be selected and used is RNA-dependent DNA polymerase or RNA-dependent RNA polymerase.

In the present invention, information on a base of a target nucleic acid, of which information is to be obtained, can be obtained by measuring whether or not a nucleotide derivative has been incorporated into the position corresponding to the base. This determination is carried out using the electrochemical convertible portion imparted to the nucleotide derivative. That is, incorporation of the nucleotide derivative having an electrochemically convertible portion into the 3'-end of the primer or extended primer (for instance, the position "Y" in FIGS. 6A and 6B) hybridized to the target nucleic acid is determined by incorporation of the electrochemically convertible portion. For instance, when the nucleic acid to be extended (primer) is DNA, one or more types of the nucleotide derivatives exemplified below are reacted with a target DNA double-stranded with the primer.

The nucleotide derivative may be, for instance, 2'-deoxyadenosine 5'-triphosphate derivative, 21-deoxycytidine 5'-triphosphate derivative, 2'-deoxyguanosine 5'-triphosphate derivative and 2'-deoxythymidine 5'-triphosphate derivative, each of which has an electrochemically convertible portion distinguishable from each other.

By selecting the type of the nucleotide derivative to be used, information about a base can be obtained as described below.

(1) When "X1" illustrated in FIG. 6 is "A", and at least one of a 2'-deoxyadenosine 5'-triphosphate derivative, a 2'-deoxycytidine 5'-triphosphate derivative and a 2'-deoxyguanosine 5'-triphosphate derivative is added to the reaction system, no signal is measured due to the incorporation of the electrochemically convertible portion into the position "Y". Accordingly, it is concluded that a nucleotide complementary to the nucleotide added to the reaction system does not exist at "X1".

(2) On the other hand, when "X1" illustrated in FIG. 6 is "A", and at least a 2'-deoxythymidine 5'-triphosphate derivative is added to the reaction system, the 2'-deoxythymidine 5'-triphosphate derivative is incorporated into the position "Y". This incorporation of the 2'-deoxythymidine 5'-triphosphate derivative can be determined by using the electrochemically convertible portion contained therein. Accordingly, it is concluded that "X1" is "A".

When the nucleic acid to be extended is RNA, at least one or more of the following derivatives are used as a nucleotide derivative: an adenosine 5'-triphosphate derivative, a cytidine 5'-triphosphate derivative, a guanosine 5'-triphosphate derivative and a uridine 5'-triphosphate derivative, each having a substituent for measurement, each of which has an electrochemically convertible portion distinguishable from each other.

The electrochemically convertible portion imparted to the nucleotide derivative causes a structure change according to the electrochemical conversion thereof. This structure change allows resumption of the extension reaction by the polymerase part of the polymerase-immobilized electrode which was stopped. Preferable structure change is irreversible elimination of the substituent including the electrochemically convertible portion from the nucleotide derivative.

Next, the nucleotide derivative having an electrochemically convertible portion is described. In the present invention, "the electrochemically convertible portion" means, for instance, an atom or an atomic group bonded to any atom constituting a nucleoside 5'-triphosphate. Accordingly, a nucleotide having the electrochemically convertible portion has the following properties (1) to (3):
(1) it can form a phosphate bonding with a hydroxyl group of the 3'-end of a primer or extended primer that is forming a complementarily pair with a target nucleic acid, by the enzymatic action of a polymerase;
(2) After forming a phosphate bonding with the hydroxyl group at the 3' end of the primer or extended primer as a result of (1), it inhibits further phosphate bonding formation with another nucleoside 5'-triphosphate derivative by the polymerase. In other words, the nucleotide derivative to be used in the present invention has a capping function; and
(3) It has a Portion Electrochemically Reducible or Oxidizable.

In addition to the above described properties (1) to (3), the nucleotide derivative preferably has a property (4).
(4) It can form another phosphate bonding by the action of the polymerase after elimination, substitution or addition reaction is caused by electrochemical reduction or oxidization.

Capping by the electrochemically convertible portion is classified into the electrochemically removal leaving group and the electrochemically replaceable substituent group, according to the difference in the electrochemical properties.

Capping in both classes can be used in the present invention as long as it satisfies the above described properties (1) to (3) ((4) can also be included). The electrochemically removable leaving group is an atom or an atomic group that is removed by two-electron reduction, such as R2 in Equation 1 or R6 in Equation 3; or it is an atom or an atomic group that is removed by two-electron oxidation, such as R4 in Equation 2 or R8 in Equation 4.

(Equation 1)

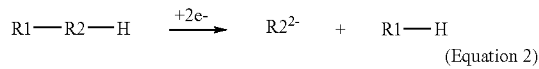

(Equation 2)

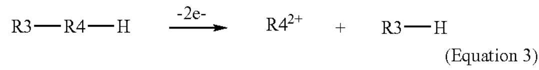

(Equation 3)

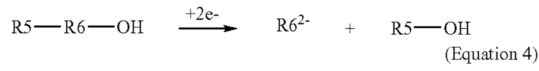

(Equation 4)

$$R7{-}R8{-}OH \xrightarrow{-2e^-} R8^{2+} + R7{-}OH$$

In the above equations, R1, R3, R5 and R7 each represents a nucleotide; and R2, R4, R6 and R8 each represents an electrochemically removable leaving group. An example of the leaving group is a group containing a typical metal such as boron and a group containing a transition organometallic complex.

An electrochemically removable substituent group is an atom or an atomic group that is removed as a radical or an anion by one-electron reduction, such as R10 in Equation 5 and Equation 6; or an atom or an atomic group that is removed as a radical or a cation by one-electron oxidation, such as R12 in Equation 7 and Equation 8.

(Equation 5)

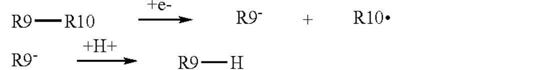

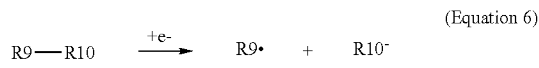

(Equation 6)

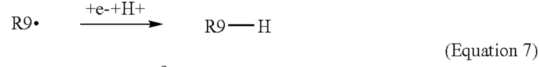

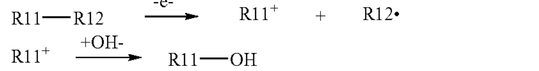

(Equation 7)

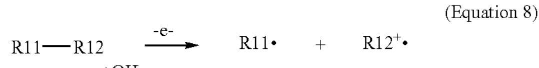

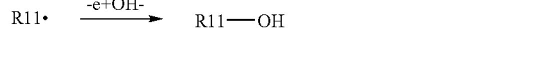

(Equation 8)

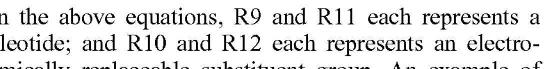

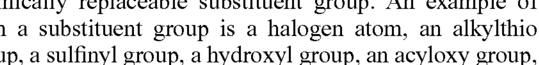

In the above equations, R9 and R11 each represents a nucleotide; and R10 and R12 each represents an electrochemically replaceable substituent group. An example of such a substituent group is a halogen atom, an alkylthio group, a sulfinyl group, a hydroxyl group, an acyloxy group, an amino group, a peroxidized group or a sulfonium group. Also the substituent group may be an organometallic complex, a nitroxy group, a 2,2,6,6-tetramethyl-1-piperidinyloxyl (TEMPO) group, a hydroquinolyl group, a methoxyquinolyl group or a phenothiazil group.

A nucleotide derivative is a nucleoside 5'-triphosphate modified with the above described electrochemically removable leaving group or an electrochemically replaceable substituent group. Specifically, the nucleotide derivative is selected according to the type of the polymerase part constituting a polymerase-immobilized electrode of the present invention. When the polymerase is DNA-dependent DNA polymerase or RNA-dependent DNA polymerase, at least one of the following four derivatives is used:

2'-deoxyadenosine 5'-triphosphate derivative (dATP derivative),

2'-deoxycytidine 5'-triphosphate derivative (dCTP derivative),

2'-deoxyguanosine 5'-triphosphate derivative (dGTP derivative) and

2'-deoxythymidine 5'-triphosphate derivative (dTTP derivative).

On the other hand, when the polymerase part constituting a polymerase-immobilized electrode of the present invention is DNA-dependent RNA polymerase or RNA-dependent RNA polymerase, at least one of the following four derivatives is used:

adenosine 5'-triphosphate derivative (ATP derivative), cytidine 5'-triphosphate derivative (CTP derivative), guanosine 5'-triphosphate derivative (GTP derivative) and uridine 5'-triphosphate derivative (UTP derivative).

The electrochemically removable leaving group is bonded to an atom constituting the nucleotide moeity, e.g., R1 in Equation 1 or R3 in Equation 2, which atom is not limited in particular as long as the above described capping properties (1) to (4) are satisfied.

Such an atom may be, for instance, the carbon atom at the 1'-position, 2'-position or the 4'-position, or the oxygen atom of the hydroxyl group at the 3'-position of the deoxyribose ring in the case of 2'-deoxyadenosine 5'-triphosphate (dATP), 2'-deoxycytidine 5'-triphosphate (dCTP), 2'-deoxyguanosine 5'-triphosphate (dGTP) and 2'-deoxythymidine 5'-triphosphate (dTTP); and also it may be the oxygen atom of the hydroxyl group at the 2'-position or the 3'-position of the ribose ring in the case of adenosine 5'-triphosphate (ATP), cytidine 5'-triphosphate (CTP), guanosine 5'-triphosphate (GTP) and uridine 5'-triphosphate (UTP).

When such an atom is a member of R5 in Equation 3 or R7 in Equation 4, the atom is not limited in particular as long as the above described capping properties (1) to (4) are all satisfied. Such an atom may be, for instance, the 3'-carbon of the deoxyribose ring in the case of dATP, dCTP, dGTP and dTTP; and the 2'-carbon and the 3'-carbon of the ribose ring in the case of ATP, CTP, GTP and UTP.

The electrochemically replaceable substituent group is bonded to an atom, e.g., a member of R9 in Equation 5 and Equation 6, it is not limited in particular as long as all the above described properties (1) to (4) concerning capping function are satisfied. Such an atom may be, for instance, the 1'-carbon, the 2'-carbon or the 4'-carbon or the oxygen atom of the hydroxyl group at the 3'-position of the deoxyribose ring in the case of dATP, dCTP, dGTP and dTTP, or the oxygen atom in the hydroxyl group at the 2'-position or the 3'-position of the ribose ring in the case of ATP, CTP, GTP and UTP.

When such an atom is a member of R11 in Equation 7 or Equation 8, it is not limited in particular as long as all the above described capping properties (1) to (4) are satisfied. Such an atom may be, for instance, the 3'-carbon of the deoxyribose ring in the case of dATP, dCTP, dGTP and dTTP. It may be, for instance, the 2'-carbon or the 3'-carbon of the ribose ring in the case of ATP, CTP, GTP and UTP.

The nucleotide derivative of the present invention capped by an electrochemically convertible structure to be used in the present invention can be prepared by using a nucleotide or nucleoside corresponding to the nucleotide derivative as a raw material. Specifically, the nucleotide derivative can be synthesized by the steps of: appropriately and selectively protecting the base moiety such as purine and pyrimidine and sugar hydroxyl groups except for the atom to be coupled with a capping moiety; and adding an electrochemically removable leaving group or an electrochemically replaceable substituent group to the nucleotide or nucleoside.

The electrochemically convertible structure to be used for the capping of each nucleoside 5'-triphosphate should make the nucleotide having the capping from the others as a result of electrochemical conversion thereof or the resulting structural change of the portion containing the structure. For instance, cappings for adenine (A), cytosine (C), guanine (G), thymine (T) and uracil (U) should be electrochemically reduced or oxidized at potentials different from each other. The four nucleotide derivatives may use four different substituent groups for measurement as long as the above conditions are satisfied, or they may use the same substituent group for measurement. This is because generally the potential will vary depending on the position of the capping coupling, even when the same capping is used. Furthermore, even when the same capping is introduced to the atom of the same position, the potential may differ according to the base bonded to the ribose or deoxyribose.

The potential at which the capping is electrochemically reduced or oxidized is not limited as long as it is in the potential window of an electrode system specified by the type of the electrode and the solvent to be used, but generally it is in the range of −100 V to +100 V (vs. SCE). More preferably, it can be −10 V to +10 V (vs. SCE), further preferably, about −1.2 V to +1.0 V (vs. SCE).

Analysis Method

Next are described the steps of a method of analyzing the base sequence of a nucleic acid according to the present invention. Prior to the first step in the method, a complementary pair is formed between a target nucleic acid and a primer by hybridization. A specific forming method includes the steps of: mixing the target nucleic acid with the primer; heating the mixture to destroy their secondary structures; and then cooling the mixture to a melting temperature (Tm) of the primer or lower. In addition, prior to the first step of the method of invention, the sample can be prepared to have a promoter sequence for RNA polymerase. Such a sample can be prepared by PCR amplification technique using a primer containing the promoter sequence, or by ligating the promoter sequence and the target nucleic acid, and then cloning it with the use of a suitable host.

A method for analyzing a base sequence of a nucleic acid according to the present invention comprises the steps of: preparing a sample containing a complementary pair of a target nucleic acid and a primer where a promoter sequence for RNA polymerase may be included, and a polymerase-immobilized electrode; and making the above described sample and the polymerase-immobilized electrode coexist in a solution. The sample containing the complementary pair of the target nucleic acid and the primer or the promoter sequence for RNA polymerase is captured by the polymerase part constituting the polymerase-immobilized electrode.

As described above, when the sample and the polymerase-immobilized electrode are put in the same solvent for contact and the electrode captures the sample, it is preferable to wash the electrode to remove the remaining sample not captured by the electrode. This nucleotide derivative is capped with a structure that gives different electrical signal acquired by the electrochemical measuring means in correspondence with adenine (A), cytosine (C), guanine (G) and thymine (T) or uracil (U). Of course, it is possible to cap plural nucleotides with the same structure as long as they can be distinguished. The nucleotide derivative may be, for instance, a nucleoside 5'-triphosphate derivative, a nucleoside 5'-diphosphate derivative, a nucleoside 5'-monophosphate derivative and a nucleoside 3'-phosphate derivative. In a mixture containing the polymerase-immobilized electrode and the nucleotide derivative(s), it is preferable that various nucleoside 5'-triphosphate derivatives are contained in the same concentration.

Consequently, a phosphate bonding is formed between the hydroxyl group at the 3'-end of the primer (or the extended primer) and the 5'-phosphate group of the nucleoside 5'-triphosphate derivative of which base is complementary with the first base of the target nucleic acid not pairing with the primer. In this step, pyrophosphoric acid is released.

It is known that the one-base extension reaction by polymerase usually completes within one second, especially when *E. coli* DNA polymerase III is used, it completes in one five-hundredth of a second at minimum. The above described process is illustrated in FIGS. 5 (1) to 5(3). When a sample containing a promoter sequence for RNA polymerase is used, transcription starts from a transcription start point in a downstream of a promoter.

Next, in the second step of the method for analyzing a base sequence of a nucleic acid, a voltage that gradually changes with time is applied to the polymerase-immobilized electrode, where the voltage changes from the natural potential to negative potential with reduction reaction, or it changes from the natural potential to positive potential with oxidation reaction, and the mode of the voltage change is constant increase the natural potential, or it may be a stepwise or pulse-like increase. By constantly increasing the absolute value of the potential, conversion of the nucleotide derivatives starts from the derivative requiring the smallest absolute voltage for conversion depending on the type of the capping structure of the nucleotide derivative. One example of the electrochemical reaction is illustrated in FIG. 5(4). When carrying out the electrochemical conversion of nucleotide derivatives, a supporting salt may be added, of which species or concentration would not inhibit the activity of polymerase. Such a supporting electrolyte includes $Na_2HPO_4$, $NaH_2PO_4$ and KCl. Use of $Na_2HPO_4$ or $NaH_2PO_4$ is preferable since they can act as a buffer as well.

The next step is to monitor the voltage applied in the second step and the electric current passing through the electrode system at that time. A reduction reaction or oxidation reaction is caused at a voltage depending on the species of capping, and the electric current accompanying the reaction can be monitored. The voltage applied to the electrode at the time when the current caused by the reaction is observed differs according to the type of the capping structure of the nucleotide derivative, so that the base species at the 3'-end of the extended strand can be known from the value of the voltage, and thereby the base of the target nucleic acid complementary with the extended base can be known.

When analysis of single base is required as in single nucleotide polymorphism analysis, it can be analyzed by using a primer having a sequence complementary to the target sequence from the 3' end to the nucleotide adjacent to the site to be analyzed, and the first and the second steps. The nucleoside 5'-triphosphate derivative to be used in the above step does not need to contain all base species of A, C, G and T or U, but has only to contain at least one of the bases constituting the polymorphism to be analyzed. In such a case of single nucleotide polymorphism analysis, it is not always necessary to apply periodically increasing voltage to the polymerase-immobilized electrode, but necessary only to apply a voltage required for electrochemical conversion of the nucleotide derivative used.

When it is required to sequentially analyze bases of the target nucleic acid, specifically, when determining the base sequence in a region to be analyzed, the above described first step and second step are carried out repeatedly. In this process, removal of the unreacted nucleoside 5'-triphosphate derivatives remaining in the solution is not always necessary between the first step and the second step. In addition, if the nucleotide derivative was added sufficiently in the initial stage, it is not necessary to replenish the nucleoside derivative during the repetition of the first and the second steps.

However, when a voltage is applied onto the electrode so as to electrochemically convert the cap structure of the nucleotide derivative at the 3'-end of the extended strand, free nucleoside 5'-triphosphate derivative remaining in the solution may be subjected to electrochemical conversion on the electrode. However, effect of such a false signal can be eliminated or reduced, for instance, as follows.

In general, the dielectric constant of the inner part of a protein such as polymerase is different from that of water. Accordingly, the potential required for electrochemical conversion of the cap structure of the nucleotide derivative attached to the 3'-end of the extended strand is different from the potential required for electrochemical conversion of the cap structure of a free, unreacted nucleoside 5'-triphosphate derivative remaining in the solution. By distinguishing the above difference as difference between the applied voltages, the effect of the false signal can be excluded from the detection result.

In addition, a nucleotide derivative added to the 3'-end of the extended strand is held in the vicinity of the electroconductive substrate. On the other hand, the unreacted nucleoside 5'-triphosphate derivative remaining in a solution is drifting in the solution. Thereby, both derivatives diffuse at different diffusion coefficients. Accordingly, the contribution of the false signal can be decreased, by using the difference between the diffusion coefficients. For instance, there is a method of rapidly changing applied voltage with time. Then, the nucleotide derivative captured in the vicinity of the electroconductive substrate causes an electrochemical reaction before the unreacted nucleoside 5'-triphosphate derivative remaining in the solution diffuses to and arrives at the electroconductive substrate. The difference between the diffusion coefficients can be measured by an impedance method, for instance.

Furthermore, a phosphate group in the unreacted nucleoside 5'-triphosphate derivative remaining in a solution is normally dissociated and has a negative charge under the conditions where the polymerase retains the catalytic activity. Accordingly, when a negative voltage is applied onto the electrode, for instance, so as to reduce the derivative at the end of an extended strand, the unreacted nucleoside 5'-triphosphate derivative remaining in the solution is electrostatically repelled by the electrode and cannot approach to the electrode. As a result, it is considered that a false signal essentially hardly contributes the detection result when the derivative at the end of the extended strand is reduced for detection. In addition, even when the derivative at the end of the extended strand is oxidized for detection, the contribution of the false signal can be reduced by temporarily retaining the electrode potential negative for a certain time before applying an oxidation potential, to keep the unreacted nucleoside 5'-triphosphate derivative in the solution away from the electrode.

Furthermore, when analyzing single nucleotide polymorphism, it is also effective to remove the unreacted nucleoside 5'-triphosphate derivative remaining in the solution by washing the electrode.

An information acquisition apparatus to be used in the above method to acquire base sequence information may be the following apparatus.

Information Acquisition Apparatus

An information acquisition apparatus comprises a reaction region for reacting a double-stranded sample made from a target nucleic acid and a primer with a nucleotide derivative in the presence of a polymerase-immobilized electrode; a voltage-applying section; and a section for obtaining electrical signals. The voltage-applying section (such as the first electrode including an electroconductive member) applies a voltage to the sample containing the nucleotide derivative having an electrochemically convertible portion. The section for obtaining an electrical signal such as the second electrode acquires electrical signals generated from electrochemical conversion of the part of the nucleotide derivative. The apparatus can also have an identification section for identifying the nucleotide derivative by using the signal sent from the section for obtaining the electrical signal.

EXAMPLES

In the following, the present invention will be described in more detail with reference to examples, but the method of the present invention is not limited to these examples.

Example 1

In this example, a gold substrate is used for the electroconductive substrate, a modified T7 DNA polymerase containing a polyhistidine tag fused to the cloned N terminus for the polymerase part, and a disulfide group for the anchor part. Also a π-conjugate metallic complex is used for the first electroconductive region, and a gold nanoparticle of 1.4 nm diameter is used for the second electroconductive region. A polymerase-immobilized electrode is prepared by using the polymerase unit (probe-modified polymerase) composed of the polymerase part, the anchor part, the first electroconductive region and the second electroconductive region which are linked in this order. The polymerase unit is immobilized on the gold substrate (an electroconductive substrate) by forming an Au—S bond between disulfide of the anchor part and the gold substrate. The details are as follows.

(I) Synthesis of Electroconductive Part

First, the following complex ligands are synthesized.

<1> Synthesis of Complex Ligand (1)

A complex ligand (4'-(4-anilino)-2,2':6',2"-terpyridine) expressed by the following Formula (1) is synthesized as follows:

(1)

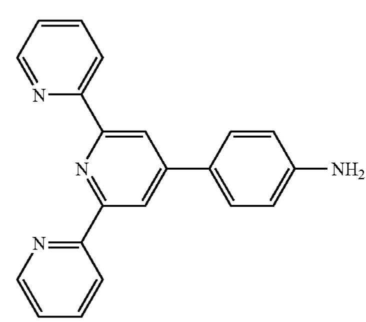

Into a 1000 ml pear-shaped flask equipped with a reflux tube, 9.7 g of 4-aminobenzaldehyde, 22 ml of 2-acetylpyridine, 75 g of ammonium acetate and 100 g of acetamide are put, and refluxed for 3 hours under the air atmosphere. The reaction solution is air-cooled, added with a solution of 50 g NaOH in 200 ml water, and refluxed for 2 hours. After the reaction solution is air-cooled, the supernatant is removed by decantation, and the residual oily solid is washed three times with water, solved with the smallest amount of hot hydrobromic acid, and left standing at room temperature for one day. The resulted dark brown precipitate is filtered, and then put into 300 mL of water, to which sodium hydrogen carbonate is added until the solution becomes alkaline. The obtained solid is subjected extraction with chloroform, and the extract is condensed by evaporation under a reduced pressure. The concentrate is then subjected to flush column chromatography using silica and chloroform, and the third fraction is concentrated by evaporation under a reduced pressure, followed by re-crystallization from a mixed solvent of chloroform and methanol to obtain the complex ligand of Formula (1).

<2> Synthesis of Complex Ligand (2)

A complex ligand expressed by the following Formula (2) is synthesized as follows.

(2)

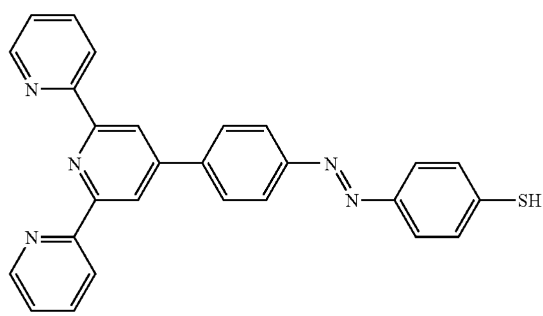

A 100 ml three-necked flask equipped with a thermometer and a reflux tube is prepared. Into the flask, 0.79 g of the complex ligand of Formula (1), 0.15 g of ammonium chloride and 5 ml of water are put, and then 0.372 g of zinc powder is slowly added with vigorous stirring using a stirrer. As the reaction proceeds automatically, the reaction temperature is adjusted to 53° C. using an ice bath to carry out the reaction for 20 minutes. Then the reaction solution is filtered, and the filtered zinc is washed with 3 ml of hot water. The filtrate and the wash are poured onto a large quantity of crushed ice to sufficiently cool the solution. To the solution containing a plenty amount of ice, 0.75 ml of concentrated sulfuric acid is added, followed by addition of 0.75 mL of a solution containing 0.17 g sodium bichromate in water and stirring for three minutes. Then the produced precipitate is collected, washed repeatedly with water, and dried using calcium chloride in a desiccator to obtain 4'-(4-nitrosobenzene)-2,2':6',2"-terpyridine.

Then in a 100 ml pear shaped flask, 1.36 g of 4'-(4-nitrosobenzene)-2,2':6',2"-terpyridine is put and dissolved with 5 mL of acetic acid. This solution is added with 0.50 g of 4-aminobenzenethiol, and stirred for 12 hours at room temperature, to which 20 ml of water is added followed by addition of sodium carbonate for neutralization, and extraction with 150 ml of chloroform. The extract is concentrated by evaporation under a reduced pressure, and the concentrate is subjected to column chromatography using an alumina filler and a mixture of chloroform and dimethylamine (20:1 mixing ratio). The obtained solution is evaporated under a reduced pressure, and dried to obtain the complex ligand of Formula (2).

<3> Synthesis of Complex Ligand (3)

A complex ligand expressed by the following Formula (3) is synthesized as follows.

(3)

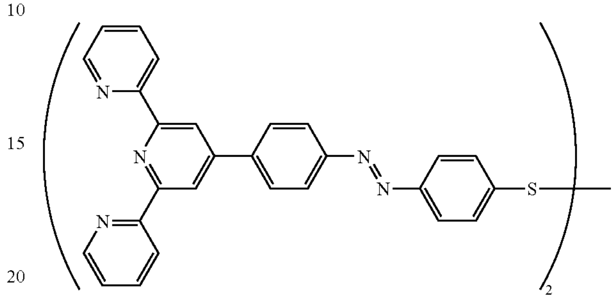

A 100 ml three-necked flask equipped with a thermometer and a reflux tube is prepared. Into the flask, 0.79 g of the complex ligand of Formula (1), 0.15 g of ammonium chloride and 5 ml of water are put, and then 0.372 g of zinc powder is slowly added with vigorous stirring using a stirrer. As the reaction proceeds automatically, the reaction temperature is adjusted to 53° C. using an ice bath to carry out the reaction for 20 minutes. Then the reaction solution is filtered, and the filtered zinc is washed with 3 ml of hot water. The filtrate and the wash are poured onto a large quantity of crushed ice to sufficiently cool the solution. To the solution containing a plenty amount of ice, 0.75 ml of concentrated sulfuric acid is added, followed by addition of 0.75 mL of a solution containing 0.17 g sodium bichromate in water and stirring for three minutes. Then the produced precipitate is collected, washed repeatedly with water, and dried using calcium chloride in a desiccator to obtain 4'-(4-nitrosobenzene)-2,2':6',2"-terpyridine.

Then in a 100 ml pear shaped flask, 1.36 g of 4'-(4-nitrosobenzene)-2,2':6',2"-terpyridine is put and dissolved with 5 mL of acetic acid. This solution is added with 0.50 g of 4,4-dithiodianiline, and stirred for 12 hours at room temperature, to which 20 ml of water is added followed by addition of sodium carbonate for neutralization, and extraction with 150 ml of chloroform. The extract is concentrated by evaporation under a reduced pressure, and the concentrate is subjected to column chromatography using an alumina filler and a mixed solvent of chloroform and dimethylamine (20:1 mixing ratio). The obtained solution is evaporated under a reduced pressure, and dried to obtain the complex ligand of Formula (3).

<4> Synthesis of Complex Ligand (4)

A complex ligand expressed by the following Formula (4) is synthesized as follows.

(4)

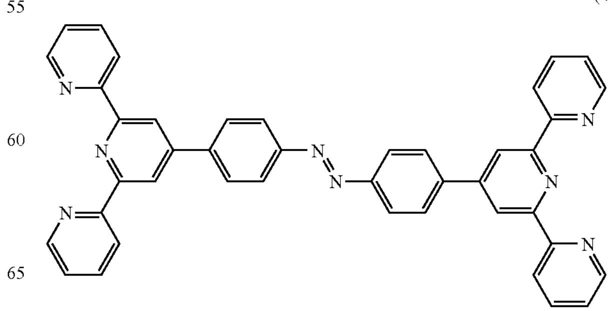

In a 100 ml pear shaped flask, 0.65 g of complex ligand of Formula (1) is put and dissolved with 5 ml of acetic acid. After addition of 0.68 g of 4'-(4-nitrosobenzene)-2,2':6',2"-terpyridine, the solution is stirred for 12 hours at room temperature. After addition of 20 ml of water and then sodium carbonate for neutralization, the solution is extracted with 150 ml of chloroform. The extract is concentrated by evaporation under a reduced pressure, and the concentrate is subjected to column chromatography using an alumina filler and a mixture of chloroform and dimethylamine (20:1 mixing ratio). The first orange eluate is collected to obtain the complex ligand of Formula (4).

(II) Preparation of Electrode

In the next step, an electrode is prepared by using complex ligands expressed by the above described Formulas (1) to (4).

<5> Bonding of Complex Ligand and Maleimido-C3-NTA

The complex ligand expressed by Formula (2) is bonded to Maleimido-C3-NTA (a product of Dojindo Laboratories Co., Ltd.) according to the supplier instruction. The Maleimido-C3-NTA is monohydrated disodium salt of N-[5-(3'-Maleimidopropylamido)-1-carboxypentyl]iminodiacetic acid.

(5)

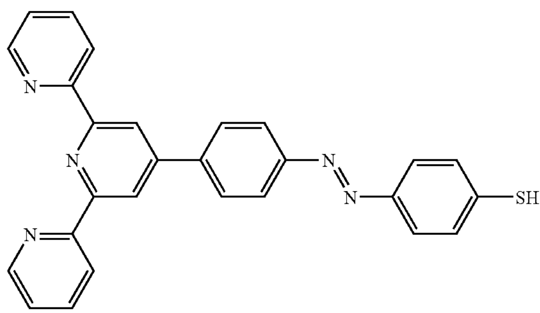

+

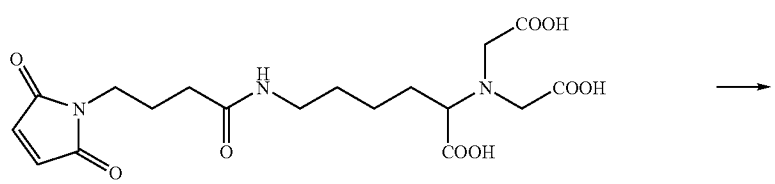

→

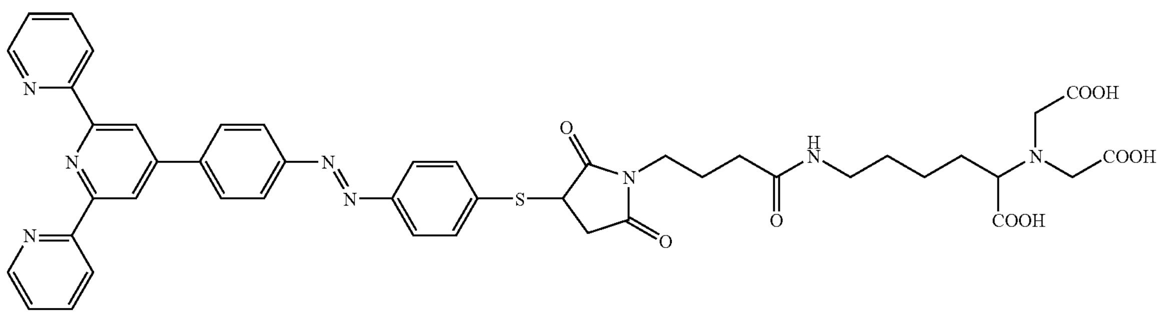

<6> Bonding of Gold Particle and Complex Ligand

The complex ligand expressed by Formula (1) and a gold particle are bonded through amido bonding according to the supplier's manual. The gold particle is Mono-Sulfo-NHS-Nanogold (trade name, a product of Nanoprobes Inc.) of 1.4 nm diameter.

(6)

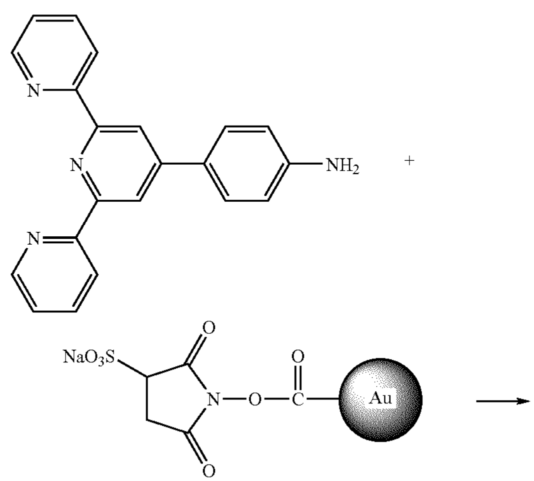

-continued

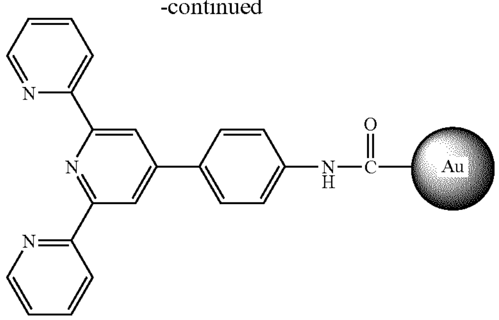

<7> Preparation of Mono-Coordinated Iron Complex

The complex ligand prepared in the step <5> is mixed with an equal mole of $Fe(BF_4)_2$ in ethyleneglycol, and the mixture is refluxed. The mono-coordinated iron complex is collected by carrying out column chromatography using an alumina column and a mixed solvent of chloroform and dimethylamine (20:1 ratio).

<8> Preparation of Di-Coordinated Iron Complex

The complex ligand expressed by Formula (3) is mixed with an equal mole of mono-coordinated iron complex prepared in the step <7>, and the mixture is refluxed. The di-coordinated iron complex is collected by carrying out column chromatography using an alumina column and a mixed solvent of chloroform and dimethylamine (20:1 ratio).

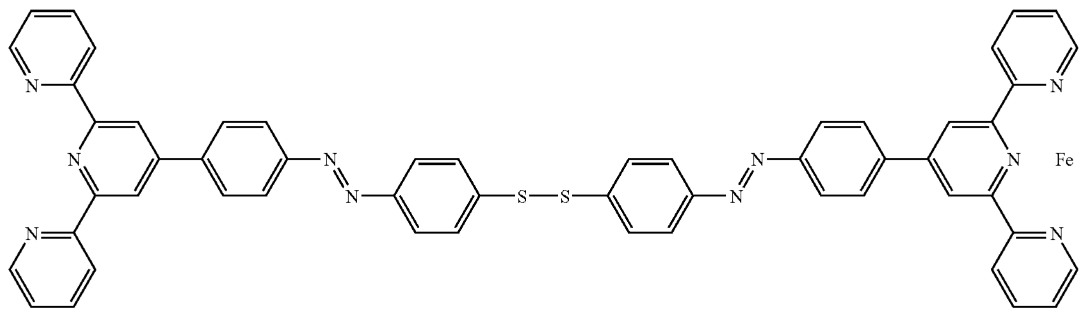

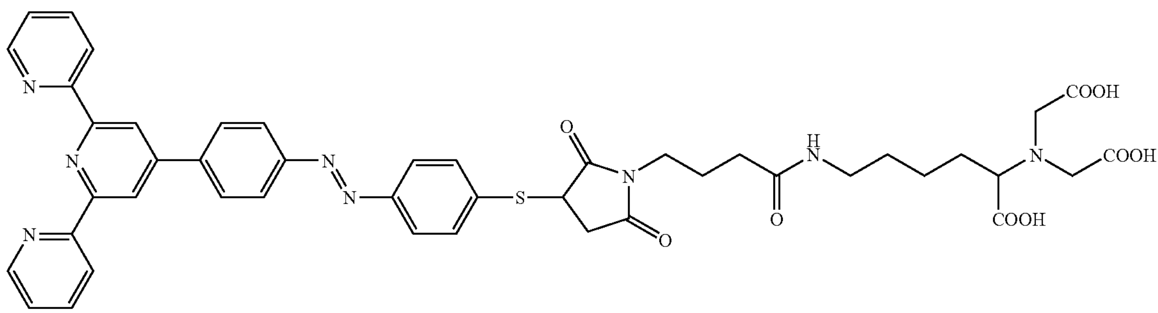

<9> Structure Preparation Composed of Anchor Part, First and Second Electroconductive Regions A gold electrode is prepared by coating a gold wire of 0.5 mm diameter with a heat-shrinkable fluorine resin tube except for the terminal 2 cm portion as a contact. The gold electrode is heated at 80° C. for six hours in an 1 M solution of potassium hydroxide, immersed in concentrated sulfuric acid for 12 hours, immersed in concentrated nitric acid for 15 minutes, then washed with extra pure water, and dried. The washed gold electrode is soaked in a solution of di-coordinated iron complex prepared in a step <8> in chloroform for five minutes, washed with chloroform, and then dried under a nitrogen stream. The dried gold electrode is soaked in a 0.1 M aqueous solution of $Fe(BF_4)_2$ for three hours, washed with water, and dried under a nitrogen stream. The gold electrode is then soaked in a solution of 0.1 M complex ligand of Formula (4) in chloroform for three hours, then washed with chloroform, and dried under a nitrogen stream. Further the dried gold electrode is immersed in a 0.1 M aqueous solution of $Fe(BF_4)_2$ for three hours, washed with water, and dried under a nitrogen stream. Then the gold electrode is immersed in a 0.1 M solution of the complex ligand of Formula (4) in chloroform for three hours, then washed with chloroform, and dried under a nitrogen stream. The dried gold electrode is further soaked in a 0.1 M aqueous solution of $Fe(BF_4)_2$ for three hours, washed with water, and dried under a nitrogen stream. Then the gold electrode is soaked in a 0.1 M solution of the complex ligand expressed by Formula (4) in chloroform for three hours, then washed with chloroform, and dried under a nitrogen stream. Further, the dried gold electrode is soaked in a 0.1 M aqueous solution of $Fe(BF_4)_2$ for three hours, washed with water, and dried under a nitrogen stream. The gold electrode is soaked in a chloroform solution containing the compound of gold nanoparticles and the complex ligand prepared in the step <6> for three hours, then washed with chloroform, and dried under a nitrogen stream. In the structure prepared as above, the distance between the anchor part (sulfide) and the gold nanoparticle being is a second electroconductive region is 9.2 nm.

<10> Preparation of Polymerase Part

First, from Enterobacteria phage T7 genome DNA (GenBank Accession No. V01146), gene 5 and DNA polymerase gene are used. PCR is carried out using the T7 genome DNA as a template, and the following two synthetic oligo DNA as primers to obtain a DNA amplification product of 1236 bp:

5'-aataatcatatgatcgtttctgacatcgaa-3' (NdeI) [SEQ ID NO: 1]; and

5'-aataatggatcctcagtggcaaatcgccca-3' (BamHI) [SEQ ID NO: 2].

The DNA amplified product is digested with restriction enzymes NdeI and BamHI, and the obtained fragment is inserted into pET-14b (a product of Novagen Corporation) digested with the same restriction enzymes. In such a manner obtained is an expression pET-14-T7g5 expressing T7 gene 5 and DNA polymerase to which a fused polyhistidine tag.

Next, to delete 28 amino acids from Lys118 to Arg145 of DNA polymerase, the corresponding portion of the T7 genome 5 is deleted, by such, an expression vector pET-14-T7g5(D28) [SEQ ID NO: 3] that expresses a modified T7 DNA polymerase having a His tag, not having 3'→5' exonuclease activity.

Thus obtained expression vector pET-14-T7g5 (D28) is used to transform *E. coli* BL21 (DE3) by a standard method. The transformants can be screened with resistance to antibiotic ampicillin.

The obtained transformant is precultured in 10 ml of LB medium containing ampicillin overnight, and then 0.2 ml of the preculture is added to fresh 100 ml of LB(Amp) medium, and shake-cultured at 170 rpm for four hours at 30° C. Subsequently, IPTG is added to the culture to a final concentration of 1 mM, and the culture is continued at 37° C. for 4 to 12 hours. The IPTG-induced transformant is collected (8,000×g, 2 minutes, 4° C.), resuspended in PBS of an 1/10 volume at 4° C. After cells are disrupted by freeze-thawing and sonication, and the solid contamination is removed by centrifugation (8,000×g, 10 minutes, 4° C.). After confirming the presence of the expressed objective protein in the supernatant by SDS-PAGE, the induced and expressed His-tag-fused protein is purified by using a nickel chelate column.

<11> Preparation of Polymerase-Immobilized Electrode

The gold electrode prepared in the step <9> is immersed in an aqueous solution containing 100 mM of $NiSO_4$ for 20 minutes to chelate nickel ion to the nitrilotriacetic acid part, and then washed with water to remove surplus nickel ions on the electrode. Then the purified sample of the modified T7 DNA polymerase in a PBS buffer system, an His-tag-fused protein prepared in the above described step <10>, is added to the electrode and left standing at 4° C. for 20 minutes. Subsequently the surplus polymerase which has not been trapped on the electrode is removed by washing the electrode with a PBS buffer solution. Then a PBS solution of *E. coli* thioredoxin (a product of Sigma) is added to the electrode, which is left standing at 4° C. for 20 minutes to activate the T7 DNA polymerase, and the surplus thioredoxin not trapped on the electrode is removed by washing the electrode with a PBS buffer solution. In the polymerase-immobilized electrode prepared as above, the distance between the anchor part and the active center of the polymerase is about 10 nm. Accordingly, the length between the anchor part and the gold nanoparticle being the second electroconductive region is approximately equal to the length between the anchor part and the active site of the polymerase.

Example 2

In this example, a gold substrate is used for the electroconductive substrate, a modified and cloned T7 DNA polymerase is used for the polymerase part, and cysteine is used for the anchor part. In addition, a double-stranded DNA is used for the first electroconductive region, and a gold nanoparticle of 1.4 nm diameter is used for the second electroconductive region. A polymerase-immobilized electrode is prepared by using the polymerase unit (probe-modified polymerase) in which the polymerase part, the anchor part, the first electroconductive region and the second electroconductive region are linked in this order. The polymerase unit is immobilized on the gold substrate (an electroconductive substrate) by forming an Au—S bond between cysteine of the anchor part and the gold substrate.

<1> Preparation of Modified T7 DNA Polymerase Having Fused Anchor Part

The following two 5'-phosphorylated synthetic oligodeoxyribonucleotides are mixed in equal amount in a TE buffer, heated and gradually cooled for annealing:

```
5'- TAGCAAAAAAAAATGTTGCGTTC -3'    [SEQ ID NO: 4]
and

5'- TAGAACAGCAACATTTTTTTTTGC-3'.   [SEQ ID NO: 5]
```

This DNA fragment is inserted into an NdeI recognition site of the expression vector pET-14-T7g5 (D28) [SEQ ID NO: 3] expressing an modified T7 DNA polymerase with fused His tag at N-terminal prepared in Example 1. Thus an expression vector pET-14-C3T7g5(D28) (SEQ ID NO:6) is prepared. The prepared expression vector pET-14-C3T7g5 (D28) is used to transform *E. coli* BL21 (DE3) by a standard method. The transformants can be screened by resistance to antibiotic ampicillin.

The obtained transformant is precultured in 10 ml of LB medium containing ampicillin overnight, and then 0.2 ml of the preculture is added to fresh 100 ml of LB(Amp) medium, and shake-cultured at 170 rpm for four hours at 30° C. Subsequently, IPTG is added to the culture to a final concentration of 1 mM, and the culture is continued at 37° C. for 4 to 12 hours. The IPTG-induced transformant is collected (8,000×g, 2 minutes, 4° C.), resuspended in PBS of an 1/10 volume at 4° C. After cells are disrupted by freeze-thawing and sonication, the solid contamination is removed by centrifugation (8,000× g, 10 minutes, 4° C.) to obtain a cell free extract. After confirming the presence of the expressed objective protein in the supernatant by SDS-PAGE, the induced and expressed His-tag-fused protein is purified by using a nickel chelate column. The polyhistidine tag at the N-terminal is cleaved and removed by thrombin.

<2> Bonding of Double-Stranded DNA as Electroconductive Part

The modified T7 DNA polymerase having an anchor part fused therein, prepared in the step <1>, has an Lys residue newly introduced into the vicinity of the N-terminal of the amino acid sequence. Consequently, the modified T7 DNA polymerase can be efficiently cross-linked to a molecule having an SH group, by using, for instance, a water-soluble crosslinking agent Sulfo-EMCS (a product of Dojindo Laboratories Co., Ltd.). Sulfo-EMCS is sodium salt of N-(6-Maleimidocaproyloxy)sulfosuccinimide.

The modified T7 DNA polymerase is cross-linked to 5'-thiolized synthetic oligodeoxyribonucleotide: 5'-acagcatcgccagtc-3' [SEQ ID NO: 7] according the supplier's manual. In addition, the terminal thiol group of the 5'-thiolized synthetic oligodeoxyribonucleotide: 5'-gactggcgatgctgt-3' [SEQ ID NO: 8] is bonded to gold particles, MONOMALEIMIDO NANOGOLD (trade name, a product of Nanoprobes Incorporated), according to the supplier's manual.

The modified T7 DNA polymerase bonded to a single stranded DNA of SEQ ID NO: 7 and the gold particle bonded to a single strand DNA of SEQ ID NO: 8 are mixed and left standing at a room temperature for hybridization to form a complementary dsDNA.

Electroconductivity is imparted to the double-stranded DNA part by intercalation of a metallo-intercalator complex into the double-stranded DNA linked to the modified T7 DNA polymerase. Specifically, an aqueous solution of dichloro(2,2':6',2"-terpyridine) platinum (II) (a product of Sigma-Aldrich Corporation, #288098) is added to the double-stranded DNA linked to the modified T7 DNA polymerase. It is known that dichloro(2,2':6',2"-terpyridine) platinum (II) binds to DNA (Peyratout et al. (1995) Inorg. Chem. 34, 4484). The bond is formed by intercalating a terpyridine ligand into DNA and subsequently forming a covalent bond, i.e., by a platination process.

<3> Coupling to Electrode

A gold electrode is prepared by coating a gold wire of 0.5 mm diameter with a heat-shrinkable fluorine resin tube except for the terminal 2 cm portion as a contact. The gold electrode is heated at 80° C. for six hours in an 1 M solution of potassium hydroxide, immersed in concentrated sulfuric acid for 12 hours, immersed in concentrated nitric acid for 15 minutes, then washed with extra pure water, and dried. Then a purified sample of the probe modified polymerase in a PBS buffer system, prepared in the above step <2>, is added to the electrode and left standing at 4° C. for 20 minutes to immobilize the polymerase onto the gold electrode using the cysteine residue near the N-terminus of the amino acid sequence. Subsequently the surplus polymerase which has not been trapped on the electrode is removed by washing the electrode with a PBS buffer solution. Then a PBS solution of *E. coli* thioredoxin (a product of Sigma) is added to the electrode, which is left standing at 4° C. for 20 minutes to activate the T7 DNA polymerase, and the surplus thioredoxin not trapped on the electrode is removed by washing the electrode with a PBS buffer solution. In the polymerase-immobilized electrode prepared as above, the distance between the anchor part and the active center of the polymerase is about 10 nm. Also the length between the anchor part and the gold nanoparticle being the second electroconductive region is about 8 nm, approximately equal to the length between the anchor part and the active site of the polymerase.

Example 3 and Comparative Example 1

Overvoltage required for converting an electrochemically convertible portion at the 3'-end of the extended strand is compared using polymerase-immobilized electrodes prepared in Example 1 and Example 2 (Example 3) and an active T7 DNA polymerase-immobilized electrode consisting of T7 DNA polymerase and thioredoxin as a control (Comparative Example 1). A tripolar cell is prepared by using a platinum wire as a counter electrode and a silver/silver chloride electrode as a reference electrode. These are linked to a potentiostat. A function generator for setting an electrode potential and a computer for measurement and data processing are further linked to the potentiostat. Voltage programmed by the function generator is applied to the polymerase-immobilized electrode through the potentiostat. The values of the applied voltage and the observed electric current are sent to the computer and are collected therein.

A synthesized oligodeoxynucleotide of SEQ ID NO: 9 is used as a model target nucleic acid. In addition, synthesized oligodeoxynucleotide of SEQ ID NO: 10 is used as a primer.

First, 10 picomoles of the target nucleic acid and 10 picomoles of the primer are mixed in 50 microliters of a TE buffer, heated at 96° C. for 20 seconds, and left standing at 25° C.

Then, the following nucleotide 5'-triphosphate derivatives which are capped by different electrochemically convertible structures corresponding to adenine (A), cytosine (C), guanine (G) and thymine (T) are used:

2'-iodo-2'-deoxyadenosine-5'-triphosphate (2'I-dATP),
2'-bromo-2'-deoxyguanosine-5'-triphosphate (2'Br-dGTP),
2'-chloro-2'-deoxythymidine-5'-triphosphate (2'Cl-dTTP), and
2-fluoro-2-deoxycytidine-5'-triphosphate (2'F-dCTP).

Some of them are commercially available (JENA BIOSCIENCE Corporation or TriLink BioTechnologies Corporation). Also they can be synthesized according to a known method described in the following documents:

Japanese Published Patent Application H07-97391,
Japanese Patent Publication H08-5908,
Gruen M. et al. (Nucleosides Nucleotides 18, 137-151 (1999)), and
"Oligonucleotide Synthesis; a practical approach" M. J. Gait (ed), IRL PRESS, (1984).

A mixture of the target nucleic acid and the primer is brought into contact with the polymerase-immobilized electrode at 37° C. for 5 minutes. Then the electrode is washed with a buffer solution A to remove the target nucleic acid and the primer not trapped on the polymerase-immobilized electrode.

Buffer Solution A:

33 mM tris-acetate buffer (pH 7.9)

66 mM potassium acetate 10 mM magnesium acetate 0.5 mM dithiothreitol 0.01% (w/v) bovine serum albumin Next, respective 50 μM aqueous solutions (pH 7.0) of 2'I-dATP, 2'Br-dGTP, 2'Cl-dTTP and 2'F-dCTP are added to the polymerase-immobilized electrode and held at 37° C. Voltage is changed with time in a repeating pattern of: a phase of sweeping the voltage at a constant speed to a negative direction on the basis of a natural potential; and a phase of holding the voltage at the natural potential. Under these conditions, by measuring the period of time before a peak current is observed after the start of the voltage sweeping, the voltages required for electrochemical conversion of each nucleotide derivative attached to the 3'-end of the extended strand can be compared.

As a result, the order of the voltage required for the electrochemical conversion of the nucleotide derivatives is 2'F-dCMP>2'Cl-dTMP>2'Br-dGMP>2'I-dAMP, not depending on the type of the polymerase-immobilized electrode. However, the polymerase-immobilized electrodes prepared in Example 1 and Example 2 show lower overvoltage than the control active T7 DNA polymerase-immobilized electrode made of T7 DNA polymerase and thioredoxin. In addition, the peak width of a reduction current for each nucleotide derivative is smaller with the polymerase-immobilized electrodes prepared in Example 1 and Example 2 than the control polymerase-immobilized electrode.

Example 4

In this example, a gold substrate is used as the electroconductive substrate, a modified and cloned T7 DNA polymerase of a thermophilic bacterium for the polymerase part, a π-conjugated metal complex for the electroconductive part, and disulfide for the anchor part. A polymerase unit (probe-modified polymerase), in which the polymerase part, the anchor part and the electroconductive region are linked in this order, is immobilized on the gold substrate (an electroconductive substrate) through the Au—S bond formed between cysteine residue of the anchor part and the gold substrate to prepare a polymerase-immobilized electrode.

<1> Preparation of Gold Electrode Having Anchor Part and Electroconductive Part Immobilized Thereon A gold electrode is prepared by coating a gold wire of 0.5 mm diameter with a heat-shrinkable fluorine resin tube except for the terminal 2 cm portion as a contact. The gold electrode is heated at 80° C. for six hours in an 1 M solution of potassium hydroxide, immersed in concentrated sulfuric acid for 12 hours, immersed in concentrated nitric acid for 15 minutes, then washed with extra pure water, and dried. The washed gold electrode is soaked in a solution of complex ligand of Formula (2) prepared in Example 1 in chloroform for five minutes, washed with chloroform, and then dried under a nitrogen stream. The dried gold electrode is then soaked in a 0.1 M aqueous solution of $Fe(BF_4)_2$ for three hours, washed with water, and dried under a nitrogen stream. The gold electrode is then soaked in a solution of 0.1 M complex ligand of Formula (5) prepared in Example 1 in chloroform for three hours, then washed with chloroform, and dried under a nitrogen stream.

(2)

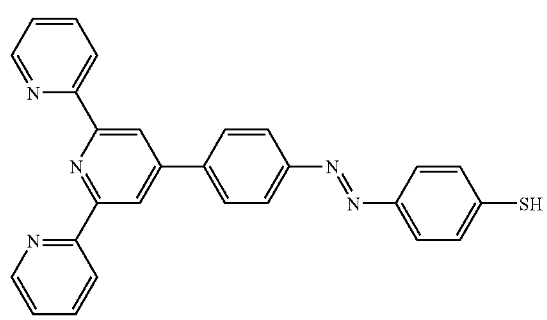

(5)

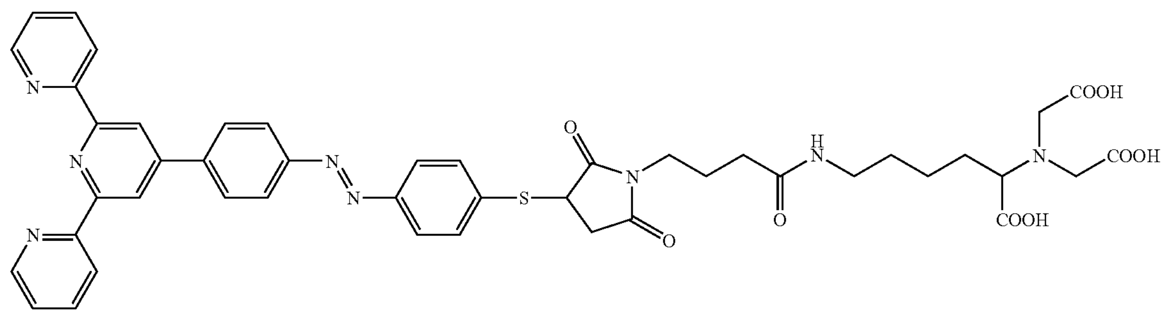

<2> Preparation of Polymerase Part

Genome DNA of thermophile *Thermus aquaticus* (ATCC 25104) is prepared by a standard method. Using this genome DNA as a template and the following synthetic oligoDNAs as primers:

```
                                          [SEQ ID NO: 13]
5'- aataatccatggccctggaggaggccccctggcccccgccggaa
g -3' (Nco I)
and

                                          [SEQ ID NO: 14]
5'- aataatgtcgactcactccttggcggagagccagtcctcccta
t -3' (Sal I)
```

PCR is carried out to obtain an amplified product of about 1,646 bp containing a sequence coding for the Stoffel fragment of DNA polymerase.

An expression vector pET-TaqDP (SEQ ID NO: 16) for the DNA polymerase Stoffel fragment (TaqDP and SEQ ID NO: 15) is prepared by cleaving the DNA amplified product using restriction enzymes NcoI and Sal I, and inserting the obtained fragment into the same restriction site of pET-45b(+) (a product of Novagen). Next, a site-specific mutation is introduced into the DNA polymerase to tether the electroconductive part near the polymerase active site. Specifically, in pET-TaqDP (SEQ ID NO: 16), CGC (956-958) are replaced by CAT, CAG (1034-1036) by CAT, and TTC (1196-1198) by CAT. The site-specific mutation is introduced into the DNA polymerase by using QuikChange (Site-Directed Mutagenesis Kit (a product of STRATAGENE) and a PCR reaction according to the supplier's protocol. Thus, an expression vector pET-mTaqDP (SEQ ID NO: 18) expressing a mutant DNA polymerase (mTaqDP, SEQ ID NO: 17) is prepared in which arginine 296, glutamine 322 and phenylalanine 367 of the DNA polymerase (TaqDP, SEQ ID NO: 15) are changed to histidine. *E. coli* BL21 (DE3) is transformed by using the expression vector pET-mTaqDP according to a standard method. Transformants can be screened by resistance to antibiotic ampicillin.

The obtained transformant is precultured in 10 ml of LB medium containing ampicillin overnight, and then 0.2 ml of the preculture is added to fresh 100 ml of LB(Amp) medium, and shake-cultured at 170 rpm for four hours at 30° C. Subsequently, IPTG is added to the culture to a final concentration of 1 mM, and the culture is continued at 37° C. for 4 to 12 hours. The IPTG-induced transformant is collected (8,000×g, 2 minutes, 4° C.), resuspended in PBS of an 1/10 volume at 4° C. After cells are disrupted by freeze-thawing and sonication, the solid contamination is removed by centrifugation (8,000×g, 10 minutes, 4° C.) to obtain a cell free extract. After confirming the presence of the expressed objective protein in the supernatant by SDS-PAGE, the induction-expressed, mutant DNA polymerase is purified as follows. The extract is placed on a hot water bath at a constant temperature of 95° C. for 20 minutes to denature and solidify the proteins from the host *E. coli*. After the contaminant proteins are removed by centrifugation (8,000×g, 10 minutes, 20° C.), the supernatant is subjected to gel-filtration chromatography using Sephadex 75 (Amersham Biosciences) equilibrated with a 50 mM Tris-HCl buffer solution (pH 8.0) containing 200 mM NaCl to obtain the fraction(s) containing the object protein.

<3> Immobilization of Polymerase Part

The gold electrode prepared in the step <9> is immersed in an aqueous solution containing 100 mM of $NiSO_4$ for 20 minutes to chelate nickel ion to the nitrilotriacetic acid part, and then washed with water to remove surplus nickel ions on the electrode. Then the purified sample of the mutated thermophila DNA polymerase in a Tris-HCl buffer system, prepared in the above step <2>, is added to the electrode and left standing at 4° C. for 20 minutes. Subsequently the surplus polymerase which has not been trapped on the electrode is removed by washing the electrode with the Tris-HCl buffer solution. In the polymerase-immobilized electrode prepared as above, the polymerase part is coordinate bonded to the end of π-conjugated metallic complex, through a histidine residue introduced into the vicinity of the active center of the polymerase.

Example 5 and Comparative Example 2

Overvoltage required for converting an electrochemically convertible portion at the 3'-end of the extended strand is measured using polymerase-immobilized electrodes prepared in Example 4. Also overvoltage required for converting an electrochemically convertible portion at the 3'-end of the extended strand is measured using the polymerase (TaqDP, SEQ ID NO:15)-immobilized electrode as a control under the same conditions as Example 5 (Comparative Example 2). These are linked to a potentiostat. A function generator for setting an electrode potential and a computer for measurement and data processing are further linked to the potentiostat. Voltage programmed by the function generator is applied to the polymerase-immobilized electrode through the potentiostat. The values of the applied voltage and the observed electric current are sent to the computer and are collected therein.

A synthesized oligodeoxynucleotide of SEQ ID NO: 9 is used as a model target nucleic acid. In addition, synthesized oligodeoxynucleotide of SEQ ID NO: 10 is used as a primer.

First, 10 picomoles of the target nucleic acid and 10 picomoles of the primer are mixed in 50 microliters of a TE buffer, heated at 96° C. for 20 seconds, and left standing at 25° C.

Then, the following nucleotide 5'-triphosphate derivatives which are capped by different electrochemically convertible structures corresponding to adenine (A), cytosine (C), guanine (G) and thymine (T) are used:

2'-iodo-2'-deoxyadenosine-5'-triphosphate (2'I-dATP),
2'-bromo-2'-deoxyguanosine-5'-triphosphate (2'Br-dGTP),
2'-chloro-2'-deoxythymidine-5'-triphosphate (2'Cl-dTTP), and
2'-fluoro-2'-deoxycytidine-5'-triphosphate (2'F-dCTP).

A mixture of the target nucleic acid and the primer is brought into contact with the polymerase-immobilized electrode at 37° C. for 5 minutes. Then the electrode is washed with a buffer solution B to remove the target nucleic acid and the primer not trapped on the polymerase-immobilized electrode.

Buffer Solution B 33 mM tris-acetate buffer (pH 7.9)
66 mM potassium acetate
10 mM magnesium acetate
0.01% (w/v) bovine serum albumin Next, respective 50 μM aqueous solutions (pH 7.0) of 2'I-dATP, 2'Br-dGTP, 2'Cl-dTTP and 2'F-dCTP are added to the polymerase-immobilized electrode and held at 70 C. Voltage is changed with time in a repeating pattern of: a phase of sweeping the voltage at a constant speed to a negative direction on the basis of a natural potential; and a phase of holding the voltage at the natural potential. Under these conditions, by measuring the period of time before a peak current is observed after the start of the voltage sweeping, the voltages required for electrochemical conversion of each nucleotide derivative attached to the 3'-end of the extended strand can be compared.

As a result, the order of the voltage required for the electrochemical conversion of the nucleotide derivatives is 2'F-dCMP>2'Cl-dTMP>2'Br-dGMP>2'I-dAMP, not depending on the type of the polymerase-immobilized electrode. However, lower overvoltage is observed with the polymerase-immobilized electrode prepared in Example 4 than with the control DNA polymerase (TaDP, SEQ ID NO:15)-immobilized electrode. In addition, the peak width of a reduction current for each nucleotide derivative is smaller with the polymerase-immobilized electrodes prepared in Example 4 than with the control polymerase-immobilized electrode.

While the present invention has been described with reference to exemplary embodiments, it is to be understood that the invention is not limited to the disclosed exemplary embodiments. The scope of following claims is to be accorded the broadest interpretation so as to encompass all such modifications and equivalent structures and functions.

This application claims the benefit of Japanese Patent Application No. 2006-170240, filed Jun. 20, 2006, which is hereby incorporated by reference herein in its entirety.

The invention claimed is:

1. A polymerase-immobilized electrode comprising an electroconductive substrate and a polymerase unit which is immobilized on the surface of the electroconductive substrate, wherein the polymerase unit comprises a polymerase part, an anchor part and an electroconductive part, which are linked in an order of the polymerase part, the anchor part and the electroconductive part, or in an order of the polymerase part, the electroconductive part and the anchor part; and the polymerase unit is immobilized on the electroconductive substrate by the anchor part;

wherein an end of the electroconductive part not immobilized on the electroconductive substrate is located in the vicinity of an active site of the polymerase part, wherein the electroconductive part is a group composed of a $\pi$-conjugated metallic complex.

2. The polymerase-immobilized electrode according to claim 1, wherein the polymerase unit comprises the polymerase part, the anchor part and the electroconductive part linked in this order, and a length from a free end of the electroconductive part to an end of the anchor part adjacent to the electroconductive part is almost the same as a length from an active site of the polymerase part to an end of the anchor part adjacent to the polymerase part.

3. The polymerase-immobilized electrode according to claim 1, wherein a polyhistidine tag and a metal to which the polyhistidine tag coordinates are present between the polymerase part and the anchor part, and the polymerase part is linked to the anchor part by coordination bonding between the polyhistidine tag and the metal to which the polyhistidine tag coordinates.

4. The polymerase-immobilized electrode according to claim 1, wherein the polymerase unit comprises the polymerase part, the electroconductive part and the anchor part linked in this order, and the electroconductive part is directly bonded to the polymerase part.

5. The polymerase-immobilized electrode according to claim 1, wherein a polyhistidine tag and a metal to which the polyhistidine tag coordinates are present between the polymerase part and the electroconductive part, and the polymerase part is linked to the electroconductive part by coordination bonding between the polyhistidine tag and the metal to which the polyhistidine tag coordinates.

6. The polymerase-immobilized electrode according to claim 1, wherein the electroconductive part contains a nucleic acid.

7. A method of obtaining base sequence information comprising the steps of:

preparing a sample of a target nucleic acid forming a double stranded portion with a primer, a polymerase-immobilized electrode and a nucleotide derivative having an electrochemically convertible part;

making the sample, the polymerase-immobilized electrode and the nucleotide derivative coexist in a solvent; and detecting whether the nucleotide derivative is introduced in the primer or not, by using an electrochemical reaction; wherein the polymerase-immobilized electrode comprises an electroconductive substrate and a polymerase unit immobilized on the surface of the electroconductive substrate, wherein the polymerase unit comprises a polymerase part, an anchor part and an electroconductive part which are linked in an order of the polymerase part, the anchor part and the electro conductive part, or in an order of the polymerase part, the electroconductive part and the anchor part; and the polymerase unit is immobilized on the electroconductive substrate by the anchor part; and an end of the electroconductive part not immobilized on the electroconductive substrate is located in the vicinity of an active site of the polymerase part, wherein the electroconductive part is a group composed of a $\pi$-conjugated metallic complex.

* * * * *